United States Patent
Shahaf et al.

(10) Patent No.: US 9,730,642 B2
(45) Date of Patent: Aug. 15, 2017

(54) NEUROPSYCHOLOGICAL SPATIOTEMPORAL PATTERN RECOGNITION

(71) Applicant: Elminda Ltd., Herzlia (IL)

(72) Inventors: Goded Shahaf, Haifa (IL); Amir B. Geva, Tel-Aviv (IL)

(73) Assignee: Elmina Ltd., Herzliya (IL)

( * ) Notice: Subject to any disclaimer, the term of this patent is extended or adjusted under 35 U.S.C. 154(b) by 0 days.

(21) Appl. No.: 14/703,913

(22) Filed: May 5, 2015

(65) Prior Publication Data

US 2015/0305685 A1    Oct. 29, 2015

Related U.S. Application Data

(62) Division of application No. 13/684,651, filed on Nov. 26, 2012, now Pat. No. 9,135,221, which is a division
(Continued)

(51) Int. Cl.
*A61B 5/00* (2006.01)
*G06K 9/00* (2006.01)
(Continued)

(52) U.S. Cl.
CPC ........ *A61B 5/7246* (2013.01); *A61B 5/04008* (2013.01); *A61B 5/04012* (2013.01);
(Continued)

(58) Field of Classification Search
CPC .. G06K 9/00543; G06K 9/6224; G06F 17/18; G06F 19/3437; A61B 5/04008; A61B 5/04012; A61B 5/0476; A61B 5/7275
See application file for complete search history.

(56) References Cited

U.S. PATENT DOCUMENTS

| 4,421,122 A | 12/1983 | Duffy |
| 4,796,199 A | 1/1989 | Hammerstrom et al. |

(Continued)

FOREIGN PATENT DOCUMENTS

| WO | WO 2007/138579 | 12/2007 |
| WO | WO 2009/069134 | 6/2009 |

(Continued)

OTHER PUBLICATIONS

Official Action Dated Jun. 26, 2015 From the US Patent and Trademark Office Re. U.S. Appl. No. 12/745,559.
(Continued)

*Primary Examiner* — Long Pham

(57) ABSTRACT

Systems and methods for identifying and analyzing neuropsychological flow patterns, include creating a knowledge base of neuropsychological flow patterns. The knowledge base is formed by obtaining signals from multiple research groups for particular behavioral processes, localizing sources of activity participating in the particular behavioral processes, identifying sets of patterns of brain activity for the behavioral processes and neuropsychologically analyzing the localized sources and the identified patterns for each of the research groups. The neuropsychological analysis includes identifying all possible pathways for the identified sets of patterns, ranking the possible pathways based on likelihood for the particular behavioral process and reducing the number of ranked possible pathways based on additional constraints. A system for comparison of obtained signals from an individual to the created knowledge base is provided. These obtained signals are then used to further update the existing knowledge base.

18 Claims, 24 Drawing Sheets

Related U.S. Application Data of application No. 12/302,271, filed as application No. PCT/IL2007/000639 on May 27, 2007, now Pat. No. 8,320,649.

(60) Provisional application No. 60/899,385, filed on Feb. 5, 2007, provisional application No. 60/808,107, filed on May 25, 2006.

(51) Int. Cl.
| | |
|---|---|
| *G06K 9/62* | (2006.01) |
| *G06F 17/18* | (2006.01) |
| *G06F 19/00* | (2011.01) |
| *A61B 5/04* | (2006.01) |
| *A61B 5/0476* | (2006.01) |

(52) U.S. Cl.
CPC .......... *A61B 5/0476* (2013.01); *A61B 5/7275* (2013.01); *G06F 17/18* (2013.01); *G06F 19/3437* (2013.01); *G06K 9/00543* (2013.01); *G06K 9/6224* (2013.01)

(56) References Cited

U.S. PATENT DOCUMENTS

| | | | |
|---|---|---|---|
| 4,862,359 | A | 8/1989 | Trivedi et al. |
| 4,983,962 | A | 1/1991 | Hammerstrom |
| 5,317,675 | A | 5/1994 | Ikehara |
| 5,333,240 | A | 7/1994 | Matsumoto et al. |
| 5,392,788 | A | 2/1995 | Hudspeth |
| 5,454,371 | A | 10/1995 | Fenster et al. |
| 6,101,241 | A | 8/2000 | Boyce et al. |
| 6,339,430 | B1 | 1/2002 | Takeshita |
| 6,516,288 | B2 | 2/2003 | Bagne |
| 6,535,201 | B1 | 3/2003 | Cooper et al. |
| 6,904,408 | B1 | 6/2005 | McCarthy et al. |
| 7,346,382 | B2 | 3/2008 | McIntyre et al. |
| 7,519,452 | B2 | 4/2009 | Seth et al. |
| 7,689,389 | B1 | 3/2010 | Mukherjee et al. |
| 7,835,581 | B2 | 11/2010 | Mathan et al. |
| 8,320,649 | B2 | 11/2012 | Shahaf et al. |
| 9,101,276 | B2 | 8/2015 | Georgopoulos |
| 2003/0068098 | A1 | 4/2003 | Rondinelli et al. |
| 2003/0087303 | A1 | 5/2003 | Patchev et al. |
| 2003/0167454 | A1 | 9/2003 | Iordanov et al. |
| 2003/0175253 | A1 | 9/2003 | Akil et al. |
| 2004/0059241 | A1 | 3/2004 | Suffin |
| 2004/0092809 | A1 | 5/2004 | DeCharms |
| 2004/0199482 | A1 | 10/2004 | Wilson |
| 2005/0005261 | A1 | 1/2005 | Severin |
| 2005/0007091 | A1 | 1/2005 | Makeig et al. |
| 2005/0009003 | A1 | 1/2005 | Deco et al. |
| 2005/0071087 | A1 | 3/2005 | Anderson |
| 2005/0118286 | A1 | 6/2005 | Suffin et al. |
| 2005/0177058 | A1* | 8/2005 | Sobell .................. A61B 5/0484 600/545 |
| 2005/0205780 | A1 | 9/2005 | Nakagaki et al. |
| 2005/0261803 | A1 | 11/2005 | Seth et al. |
| 2005/0273449 | A1 | 12/2005 | Peacock et al. |
| 2005/0283363 | A1 | 12/2005 | Weng et al. |
| 2006/0017749 | A1 | 1/2006 | McIntyre et al. |
| 2006/0089824 | A1 | 4/2006 | Siekmeier et al. |
| 2006/0106501 | A1 | 5/2006 | Gomer et al. |
| 2006/0184463 | A1 | 8/2006 | Cook et al. |
| 2006/0217781 | A1 | 9/2006 | John |
| 2007/0011118 | A1 | 1/2007 | Snook et al. |
| 2007/0043401 | A1 | 2/2007 | John |
| 2007/0094481 | A1 | 4/2007 | Snook et al. |
| 2007/0100251 | A1 | 5/2007 | Prichep |
| 2007/0106399 | A1 | 5/2007 | Korchinski |
| 2007/0106479 | A1 | 5/2007 | Geerts et al. |
| 2007/0162086 | A1 | 7/2007 | DiLorenzo |
| 2007/0191704 | A1 | 8/2007 | DeCharms |
| 2008/0091118 | A1 | 4/2008 | Georgopoulos |
| 2008/0091628 | A1 | 4/2008 | Srinivasa et al. |
| 2008/0234322 | A1 | 9/2008 | Syroid et al. |
| 2008/0236270 | A1 | 10/2008 | Denichou et al. |
| 2009/0297000 | A1 | 12/2009 | Shahaf et al. |
| 2010/0113959 | A1 | 5/2010 | Pascual-Leone et al. |
| 2010/0277489 | A1 | 11/2010 | Geisner et al. |
| 2011/0004115 | A1 | 1/2011 | Shahaf et al. |
| 2011/0004412 | A1 | 1/2011 | Shahaf et al. |
| 2011/0022548 | A1 | 1/2011 | Shahaf et al. |
| 2013/0080127 | A1 | 3/2013 | Shahaf et al. |
| 2014/0214730 | A9 | 7/2014 | Shahaf et al. |

FOREIGN PATENT DOCUMENTS

| | | |
|---|---|---|
| WO | WO 2009/069135 | 6/2009 |
| WO | WO 2009/069136 | 6/2009 |

OTHER PUBLICATIONS

Office Action Dated Aug. 30, 2015 From the Israel Patent Office Re. Application No. 206003 and Its Translation Into English.
Office Action Dated Sep. 16, 2015 From the Israel Patent Office Re. Application No. 206002 and Its Translation Into English.
Official Action Dated Feb. 1, 2016 From the US Patent and Trademark Office Re. U.S. Appl. No. 12/745,558.
Office Action Dated Mar. 7, 2016 From the Israel Patent Office Re. Application No. 241842 and Its Translation Into English.
Requisition by the Examiner Dated Apr. 28, 2016 From the Canadian Intellectual Property Office Re. Application No. 2,706,643.
Official Action Dated Jun. 10, 2016 From the US Patent and Trademark Office Re. U.S. Appl. No. 12/745,559.
Requisition by the Examiner and the Examination Search Report Dated Apr. 29, 2015 From the Canadian Intellectual Property Office Re. Application No. 2,706,643.
Communication Pursuant to Article 94(3) EPC Dated Mar. 16, 2012 From the European Patent Office Re. Application No. 07736379.4.
Communication Pursuant to Rules 70(2) and 70a(2) EPC Dated Dec. 3, 2013 From the European Patent Office Re. Application No. 08855707.9.
International Preliminary Report on Patentability Dated Jun. 10, 2010 From the International Bureau of WIPO Re. Application No. PCT/IL2008/001559.
International Preliminary Report on Patentability Dated Jun. 10, 2010 From the International Bureau of WIPO Re. Application No. PCT/IL2008/001560.
International Preliminary Report on Patentability Dated Nov. 28, 2008 From the International Bureau of WIPO on Behalf of the International Searching Authority Re.: Application No. PCT/IL2007/00639.
International Search Report and the Written Opinion Dated Nov. 6, 2007 From the International Searching Authority Re.: Application No. PCT/IL2007/00639.
International Search Report and the Written Opinion Dated Apr. 10, 2009 From the International Searching Authority Re. Application No. PCT/IL2008/001559.
International Search Report and the Written Opinion Dated Mar. 12, 2009 From the International Searching Authority Re. Application No. PCT/IL08/01560.
Notice of Allowance Dated Jul. 19, 2012 From the US Patent and Trademark Office Re. U.S. Appl. No. 12/302,271.
Notice of Allowance Dated Jan. 20, 2015 From the US Patent and Trademark Office Re. U.S. Appl. No. 13/684,651.
Office Action Dated May 15, 2014 From the Israel Patent Office Re. Application No. 195475 and Its Translation Into English.
Office Action Dated Jan. 19, 2015 From the Israel Patent Office Re. Application No. 195475.
Office Action Dated Nov. 28, 2011 From the Israel Patent Office Re. Application No. 195475 and Its Translation Into English.
Official Action Dated Apr. 1, 2015 From the US Patent and Trademark Office Re. U.S. Appl. No. 12/745,558.
Official Action Dated Mar. 1, 2013 From the US Patent and Trademark Office Re. U.S. Appl. No. 12/745,559.

(56) References Cited

OTHER PUBLICATIONS

Official Action Dated Sep. 2, 2014 From the US Patent and Trademark Office Re. U.S. Appl. No. 12/745,558.
Official Action Dated Jul. 9, 2014 From the US Patent and Trademark Office Re. U.S. Appl. No. 13/684,651.
Official Action Dated Sep. 9, 2014 From the US Patent and Trademark Office Re. U.S. Appl. No. 12/745,559.
Official Action Dated Oct. 12, 2011 From the US Patent and Trademark Office Re. U.S. Appl. No. 12/302,271.
Official Action Dated Dec. 13, 2011 From the US Patent and Trademark Office Re. U.S. Appl. No. 12/745,559.
Official Action Dated Aug. 16, 2012 From the US Patent and Trademark Office Re. U.S. Appl. No. 12/745,558.
Official Action Dated Mar. 22, 2012 From the US Patent and Trademark Office Re. U.S. Appl. No. 12/302,271.
Official Action Dated Jun. 25, 2013 From the US Patent and Trademark Office Re. U.S. Appl. No. 12/745,558.
Requisition by the Examiner Dated Oct. 17, 2013 From the Canadian Intellectual Property Office Re. Application No. 2,653,513.
Response Dated Nov. 10, 2011 to Official Action of Oct. 11, 2011 From the US Patent and Trademark Office Re. U.S. Appl. No. 12/745,559.
Response Dated Jul. 27, 2011 to Official Action of Jun. 28, 2011 From the US Patent and Trademark Office Re. U.S. Appl. No. 12/302,271.
Restriction Official Action Dated Oct. 11, 2011 From the US Patent and Trademark Office Re. U.S. Appl. No. 12/745,559.
Restriction Official Action Dated Apr. 25, 2014 From the US Patent and Trademark Office Re. U.S. Appl. No. 13/684,651.
Restriction Official Action Dated Jun. 28, 2011 From the US Patent and Trademark Office Re. U.S. Appl. No. 12/302,271.
Supplementary European Search Report and the European Search Opinion Dated Nov. 14, 2013 From the European Patent Office Re. Application No. 08855707.9.
Translation Dated Feb. 1, 2015 of Office Action Dated Jan. 19, 2015 From the Israel Patent Office Re. Application No. 195475.
Adeli et al. "Alzheimer's Disease and Models of Computation: Imaging, Classification, and Neural Models", Journal of Alzheimer's Disease, 7: 187-199, 2005.
Baumgartner et al. "Ranking fMRI Time Courses by Minimum Spanning Trees: Assessing Coactivation in fMRI", Neuroimage, XP002456531, 13(4): 734-42, Apr. 2001. Abstract.
Boyd et al. "Answering the Call: The Influence of Neuroimaging and Electrophysiological Evidence on Rehabilitation", Physical Therapy, 87(6): 684-703, Jun. 2007. p. 684, Para 1, p. 685, Para 3—p. 686, col. 1, Para 1, p. 688, col. 3, Para 2, p. 699, col. 3, Para 1, 2.
Boyd et al. "Answering the Call: The Influence of Neuroimaging and Electrophysiological Evidence on Rehabilitation", Physical Therapy, XP055086886, 87(6): 684-703, Jun. 2007.
Giese et al. "Neural Mechanisms for the Recognition of Biological Movements", Nature Reviews Neuroscience, 4: 179-192, Mar. 2003.
Lee et al. "Large-Scale Neural Models and Dynamic Causal Modelling", NeuroImage, 30 (2006): 1243-1254.
Reijneveld et al. "The Application of Graph Theoretical Analysis to Complex Networks in the Brain", Clinical Neurophysiology, XP022295008, 118(11): 2317-2331, Oct. 11, 2007.
Rowe et al. "Multivariate Statistical Analysis in fMRI", IEEE Engineering in Medicine and Biology Magazine, XP002456532, 25(2): 60-64, Mar. 2006. p. 62-64, Section "Connectivity Analysis", Figs.5, 6.
Sloan et al. "Neurophysiology and SPECT Cerebral Blood Flow Patterns in Dementia", Electroencephalography and Clinical Neurophysiology, 91: 163-170, 1994.
Thirion "Analyse de Donn?es d'IRM Fonctionnelle Statistiques, Information et Dynamique. [FMRI Data Analysis: Statistics, Information and Dynamics]", Thesis Submitted for the Degree of Doctor of Science, Inria Sophia-Antipolis [Online], XP002456533, p. 161-179, Oct. 1, 2003. Retrieved From the Internet.
Office Action Dated Jan. 28, 2016 From the Israel Patent Office Re. Application No. 206002 and Its Translation Into English.
Summons to Attend Oral Proceedings Pursuant to Rule 115(1) EPC Dated Sep. 13, 2016 From the European Patent Office Re. Application No. 07736379.4.
Official Action Dated Sep. 28, 2016 From the US Patent and Trademark Office Re. U.S. Appl. No. 12/745,558.
Communication Pursuant to Article 94(3) EPC Dated Jun. 17, 2015 From the European Patent Office Re. Application No. 07736379.4.
Aurlien et al. "A New Way of Building a Database of EEG Findings", Clinical Neurophysiology, XP055195185, 110: 986-995, Feb. 1999.
Decision to Refuse a European Patent Application dated Mar. 27, 2017 From the European Patent Office Re. Application No. 07736379.4. (8 Pages).
Office Action dated May 23, 2017 From the Israel Patent Office Re. Application No. 206003 and Its Translation Into English. (7 Pages).
Official Action dated Jun. 6, 2017 From the U.S. Appl. No. 12/745,558. (31 Pages).
Official Action dated Mar. 31, 2017 From the U.S. Appl. No. 12/745,559. (25 Pages).
Provision of a Copy of the Minutes in Accordance With Rule 124(4) EPC dated Mar. 27, 2017 From the European Patent Office Re. Application No. 07736379.4. (6 Pages).
Requisition by the Examiner dated Apr. 3, 2017 From the Canadian Intellectual Property Office Re. Application No. 2,706,643.

\* cited by examiner

NEUROPSYCHOLOGICAL SPATIOTEMPORAL PATTERN RECOGNITION

RELATED APPLICATIONS

This application is a division of U.S. patent application Ser. No. 13/684,651 filed on Nov. 26, 2012, which is a division of U.S. patent application Ser. No. 12/302,271 filed on May 26, 2009, now U.S. Pat. No. 8,320,649, which is a National Phase of PCT Patent Application No. PCT/IL2007/000639 having International Filing Date of May 27, 2007, which claims the benefit of priority of U.S. Provisional Patent Application Nos. 60/899,385 filed on Feb. 5, 2007 and 60/808,107 filed on May 25, 2006. The contents of the above applications are all incorporated by reference as if fully set forth herein in their entirety.

FIELD OF THE INVENTION

The present invention relates to methods of functional brain imaging and, more particularly, to methods for modeling and/or diagnosing particular neuropsychological functions via spatiotemporal flow patterns among functional brain regions.

BACKGROUND OF THE INVENTION

It is known in the field of neuropsychology that behavioral functions are based upon flow among various functional regions in the brain, involving specific spatiotemporal flow patterns. Likewise, behavioral pathologies are often indicated by a change in the patterns of flow. The specific spatiotemporal pattern underlying a certain behavioral function or pathology is composed of functional brain regions, which are often active for many tens of milliseconds and more. The flow of activity among those regions is often synchronization-based, even at the millisecond level and sometimes with specific time delays.

Currently, methods for relating behavioral functions to their underlying localized brain activities usually identify discrete participating regions. Although it is known that multiple regions play a role and that the flow from one region to another is important, there are currently very few methods for patterning this flow and relating the patterns to particular tasks, and those methods which do attempt to pattern the flow do not seem to yield sufficiently sensitive and specific identification of the flow patterns underlying specific behavioral functions and pathologies.

SUMMARY OF THE INVENTION

There is provided a method for establishing a knowledge base of neuropsychological flow patterns. The method includes obtaining signals from multiple research groups for a particular behavioral process, localizing sources of activity participating in the particular behavioral functions for the research groups, identifying sets of patterns of brain activity for the behavioral functions for the research groups, neuropsychologically analyzing the localized sources and the identified patterns for each of the research groups, wherein neuropsychologically analyzing includes identifying a plurality of possible pathways for the identified sets of patterns, ranking the possible pathways based on likelihood for the particular behavioral process, and reducing the number of ranked possible pathways based on additional constraints. After neuropsychologically analyzing the localized sources, the method further includes creating a set of flow patterns from the neuropsychologically analyzed sources and patterns, for each of the research groups and creating a knowledge base of the flow patterns, wherein the knowledge base is then used as a constraint for the reducing.

There is provided, in accordance with additional embodiments of the present invention, a system for neuropsychological brain activity analysis. The system includes a signal collector for collecting signals from a testing subject, a processor having a pattern generator for generating patterns based on the collected signals and a neuropsychological analyzer for translating the generated patterns into neuropsychologically accurate pathways for particular tasks. The system further includes a flow pattern knowledge base having previously determined neuropsychological pathways and a pattern comparator for comparing the collected signals to the flow pattern knowledge base, and an output module for presenting results of the comparison.

There is provided, in accordance with additional embodiments of the present invention, a knowledge base of flow patterns comprised of at least one set of flow patterns corresponding to a neuropsychological behavior. The set of flow patterns is established based on identification and neuropsychological analysis of patterns of brain activity from multiple subjects during performance of the neuropsychological behavior, and the set may be compared to a flow pattern obtained from an individual subject. Moreover, the knowledge base may be used to further enhance the identification and neuropsychological analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWING(S)

The above and further advantages of the present invention may be better understood by referring to the following description in conjunction with the accompanying drawings in which.

Figure 1:
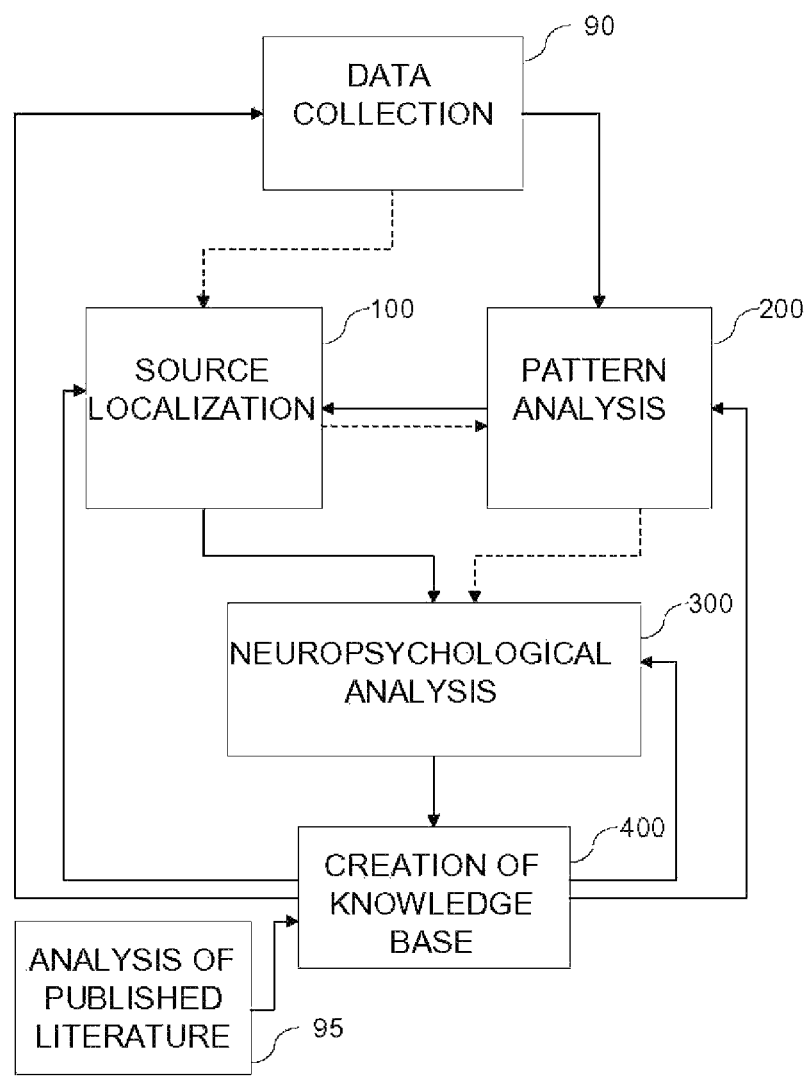
FIG. 1 is a flow chart diagram illustration of an overview of a method of patterning flow in the brain, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to methods for spatiotemporal patterning of neuropsychological processes. The principles and operation of methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

The present invention is directed to a tool which can be used for individual subjects, to analyze their brain activity so as to identify neuropsychological patterns related to behavior, to correlate these identified patterns with particular pathological or non-pathological states, and to aid in therapeutic methods for treating pathologies associated with the identified patterns. Methods for creating such a tool are described first. Methods for using the tool with individual subjects are then described in a later section.

Reference is now made to FIG. 1, which is a flow chart diagram illustration of an overview of a method of patterning flow in the brain, in accordance with embodiments of the present invention. The end result of this method is the creation of a knowledge base, which can then be used as reference for later individual trials on subjects. In order to identify flow patterns and create the knowledge base, first data is collected (step 90) from multiple subjects. Data collection is done for a particular behavioral function or pathology by collecting data from target groups as well as from control groups. The data collection could be based upon a set of computerized tasks each of the subjects performs, wherein the tasks may include relevant types of stimuli and responses, or data collection may be done during "spontaneous" activity with no such specific task. It should be noted that once the initial knowledge base entry is formed for a specific behavioral function or pathology, data may be continually added to improve the accuracy of the knowledge base. After data is collected for a specific behavioral function or pathology from the relevant target and control groups, one of two analysis lines may be taken. In one embodiment, the sources in the brain for each activity are first localized (step 100) from the sampled activity of each subject, as shown with dotted arrows. Source localization involves identifying, from the sampled activity, regions of the brain which underlie it at specific times. Source localization may be performed in various ways, including known methods and novel ones. In some cases, the source localization method will yield various possible solutions, which may then be sorted according to their neurophysiological and neuropsychological likelihood. The next step in this embodiment is pattern analysis (step 200), wherein the localized sources are arranged as a time-series for each subject. The elementary events for the time-series could be filtered waveforms, wavelets, markers of wave amplitudes, etc. It should be noted that in this embodiment the focus upon regions which repetitively participate in patterns over many subjects in research groups enables correction of inaccurate source localizations. For example, if an activity is "smeared" in one subject from region A to a neighboring region B, but consistently occurs in region A on many subjects of the research group, only region A will occur in a pattern.

In another embodiment, pattern analysis (step 200) is done prior to source localization (step 100), on the data collected at the initial step. Then, source localization (step 100) is done for activities which participate in patterns of interest in order to provide a context for the next step, which is neuropsychological analysis (step 300). Once patterns are related to a behavioral function or pathology or to common behavioral sub-functions, which are shared by various higher level behavioral functions (such as, for example, working memory, attention, etc.), the patterns are analyzed (step 300) in neuropsychological terms. As will be presented, this analysis is used to correct possible inaccuracies in the source localizations and/or the pattern generation. The pattern analysis further leads to creation (step 400) of a knowledge base of entries of known patterns relating to behavioral functions and pathologies or common sub-functions. The knowledge base is also based upon analysis (step 95) of published neuropsychological literature. The analysis of published neuropsychological literature is unique in that it includes a description of possible flow patterns among functional brain regions relating to specific behavioral functions, sub-functions or pathologies. Currently, such functional flow information is not generally available in the literature, which usually describes the participation of certain regions in a certain behavioral function or pathology, often without reference to their functional flow relations with other regions in the specific function or pathology or in alternative functions. The knowledge base, in turn, enables improved source localization and analysis of spatiotemporal patterns, by posing constraints regarding possible flow patterns among functional regions. This entire process of improved pattern analysis and localization is automated by evaluating the likelihood of alternative localizations and patterns based on this neuropsychological knowledge base.

Figure 2:
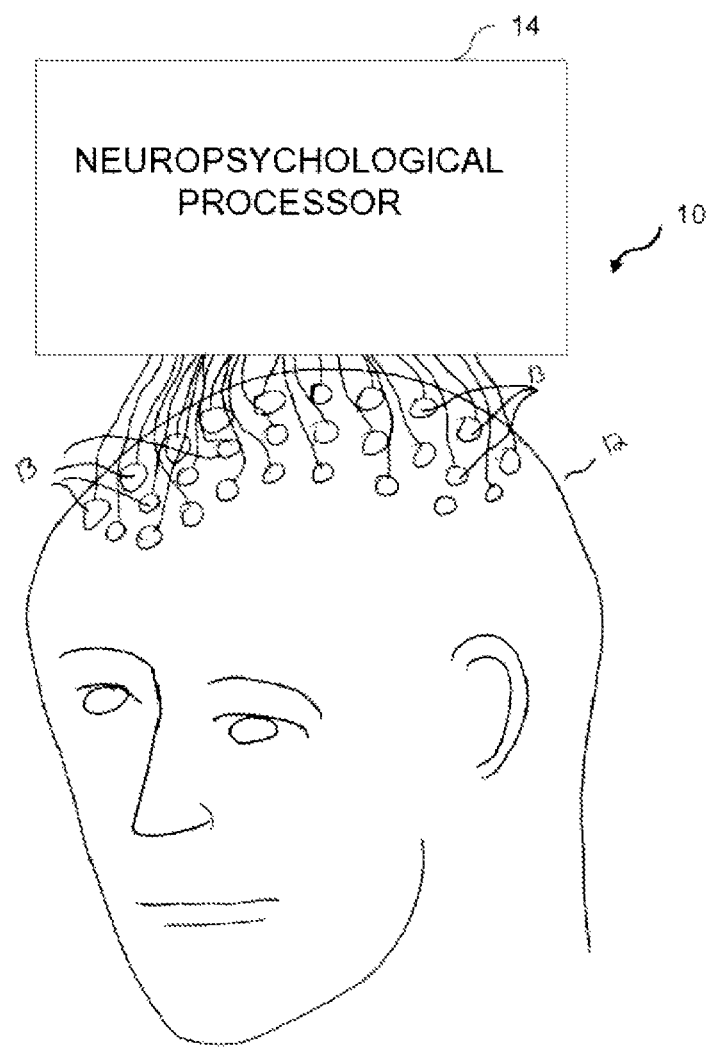
FIG. 2 is a schematic illustration of a system that can be used for data collection in accordance with embodiments of the present invention.

Reference is now made to FIG. 2, which is a schematic illustration of a system 10 that can be used for data collection (step 90) in accordance with embodiments of the present invention. A subject 12 has an array of electrodes 13 placed on his head. Each of electrodes 13 is in electrical communication with a neuropsychological processor 14, the details of which will be described hereinbelow. The electrical communication between electrodes 13 and neuropsychological processor 14 can be via wires, as shown in FIG. 2, but can also be wireless. Electrodes 13 may be placed according to known methods. For example, a 10-20 EEG system may be used, with activity recording from multiple locations, with a reference electrode and a ground. In some embodiments, eye movements (EOG) and muscle movements are recorded as well. Subject 12 is presented with a stimulus or a set of stimuli, and activity is recorded during a response to the stimulus or stimuli. In alternative embodiments, subject 12 is not presented with particular stimuli and responses, and activity is recorded during "spontaneous activity" or during particular activities. Many such protocols of stimuli, stimuli-responses, action-related and "spontaneous" activity are known in the art, and may include any stimulus-response neuropsychological tests such as Stroop, Wis., etc; tests may include stimulus-only based tests such as mismatch negativity, BERA, etc; they may include response-only based tests, such as saccade analysis, MRP, etc; and they may include "spontaneous" activity. Activity is sampled for multiple subjects of the target and control groups. In some embodiments, multiple repetitions are averaged and in other embodiments, only single trials are used. In some embodiments, continuous input may be used. The sampled activity is then sent to neuropsychological processor 14, where the data are amplified, digitized, recorded and used in an algorithm to determine flow patterns and interpret their neuropsychological meaning.

For the purposes of the present invention, any known method for sampling the brain may be used, including MEG, fMRI, PET, optical imaging or any other noninvasive or invasive method and/or combinations thereof. However, the use of EEG or event related potential (ERP) for sampling as it relates to flow patterning has the advantage of high temporal resolution (in the millisecond range) (as does MEG, but which is significantly more expensive). While the tradeoff is in spatial resolution, from a neurophysiological perspective, and while looking for temporal patterns, the temporal resolution is more critical. Spatial resolution of several $cm^2$ may be very informative in neuropsychological terms. Furthermore, neighboring regions in the brain generally tend to act in a more synchronous manner and therefore compromise in spatial resolution is often bearable.

Figure 3:
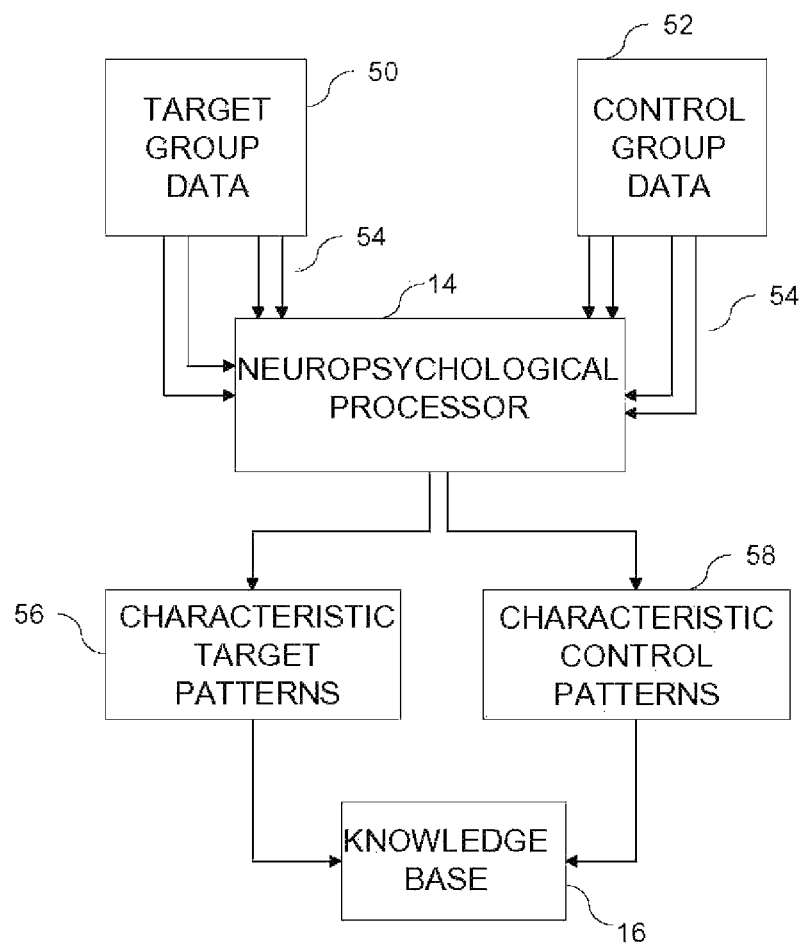
FIG. 3 is a block diagram illustration showing the formation of a database of data from multiple subjects from different research groups.

Reference is now made to FIG. 3, which is a block diagram illustration showing the formation of a database of data from multiple subjects from the different research groups. A research group is defined as a group of subjects with similar behaviors. The behaviors may be actions or activities which are performed in a specific way due to a pathological condition, or the behaviors may be non-pathological actions which the subjects are requested to perform, for example. A research group may also include a control group for comparison with a group having or suspected of having a certain pathological condition or a control group for comparison with a group performing the action. Activity data of subjects are grouped according to research groups (for example, a target group and a control group, as depicted in FIG. 3). Data 50, 52 from each of the research groups are sent to neuropsychological processor 14. Although only two research groups are depicted in FIG. 3, it should be readily apparent that multiple research groups may be included. Data from multiple subjects are needed for each research group for generation of patterns by neuropsychological processor 14, as indicated by multiple arrows 54. Neuropsychological processor 14 identifies patterns that are repetitive over different subjects in the different research groups based on the entered data. Thus, the output from neuropsychological processor 14 is a set of characteristic research group patterns, such as characteristic target patterns 56 and characteristic control patterns 58 as depicted in FIG. 3. These characteristic patterns are sent to knowledge base 16 and may be used for later comparison with data from individual subjects. It should be apparent that this is a dynamic system, and that as more patterns are entered, either during research or during testing of individual subjects, the more robust the resulting characteristic patterns will be. Furthermore, knowledge base 16 can then be used to help determine flow patterns in individual subjects, by sending the known information regarding a particular activity to a flow pattern comparator, as will be described in greater detail hereinbelow.

Figure 4:
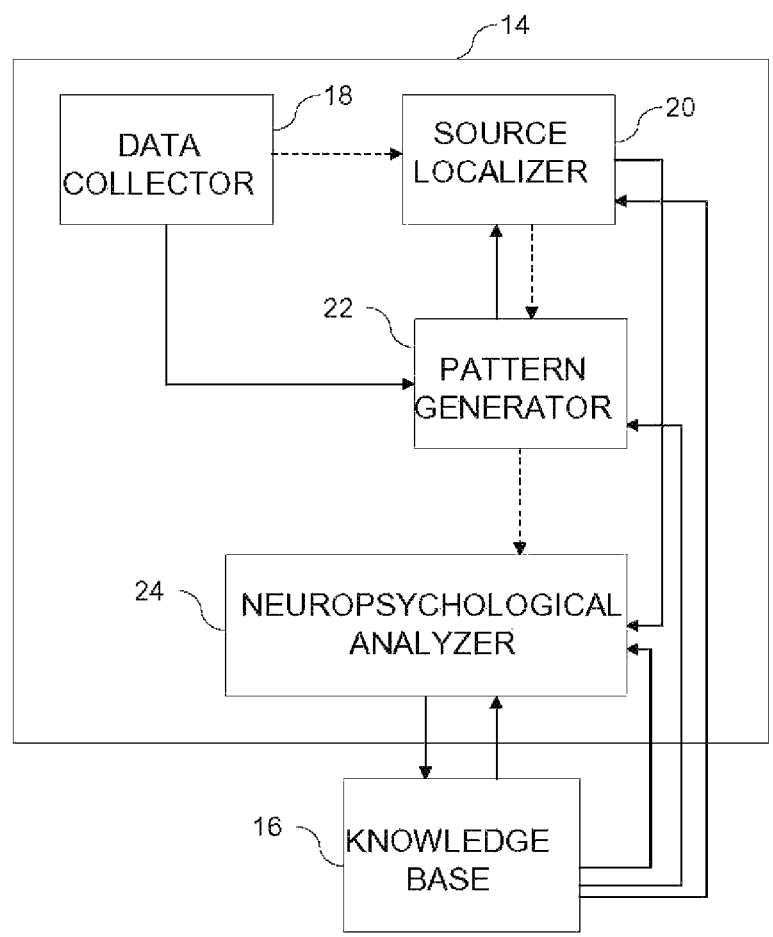
FIG. 4 is a block diagram illustration of a neuropsychological processor, showing its individual components.

Reference is now made to FIG. 4, which is a block diagram illustration of neuropsychological processor 14 showing its individual components. Neuropsychological processor 14 includes a data collector 18, a source localizer 20, a pattern generator 22, and a neuropsychological analyzer 24. Data collector 18 includes a receiver for receiving sampled activity from electrodes 13. In one embodiment, shown by the broken arrows, the activity is first processed by source localizer 20 in such a way that individual locations can be identified. These identified locations are then sent to pattern generator 22, which identifies a pattern of flow among the localized sources for the various research groups based on the recordings from electrodes 13. These patterns are then sent to neuropsychological analyzer 24, which analyzes them in neuropsychological terms by matching with the knowledge base. This matching analysis will be described in further detail herein below. In an alternative embodiment, shown by unbroken arrows, the sampled activity is first sent to pattern generator 22, which identifies spatiotemporal patterns among the various electrodes for the various research groups. These identified patterns are then sent to source localizer 20 so as to identify active locations within the brain for each activity. The identified patterns, which are identified in terms of their localized brain regions, are then sent to neuropsychological analyzer 24. In both embodiments, the analyzed neuropsychological flow patterns can then be sent to knowledge base 16, to further build up, update and correct the library of patterns for each behavioral function and sub-function. The identified patterns of the neuropsychological analysis are further used to improve the results of the previous source localization and pattern generation by selecting among possibilities and by offering likely corrections.

The individual components of neuropsychological processor 14 and methods of use thereof are now described. As a first step, data collector 18 collects activity from electrodes 13. For example, many different waveforms of varying frequencies and amplitudes over time will be collected for each electrode. All waveforms at all frequencies could then be analyzed at each electrode. Although this method of inclusion of all waveforms at the various frequencies is suggested, it should be readily apparent that other specific waveform definitions with their corresponding analysis methods may be used as well, such as, for example, space filters, blind source separation, or wavelets. Methods for frequency separation are known to those skilled in the art, and may be based on, for example, Fourier transform or different wavelet transforms. The separated bands can then be analyzed for identification of peak areas of activity in the brain, or analyzed in any other manner to form a discrete time-series of events at the various electrodes. Combinations of synchronous activities at different frequencies may also be used, and may help in description of the waveform and the neural pattern. It should be noted that other methods of activity analysis, which are not waveform based are also possible.

Figure 5:
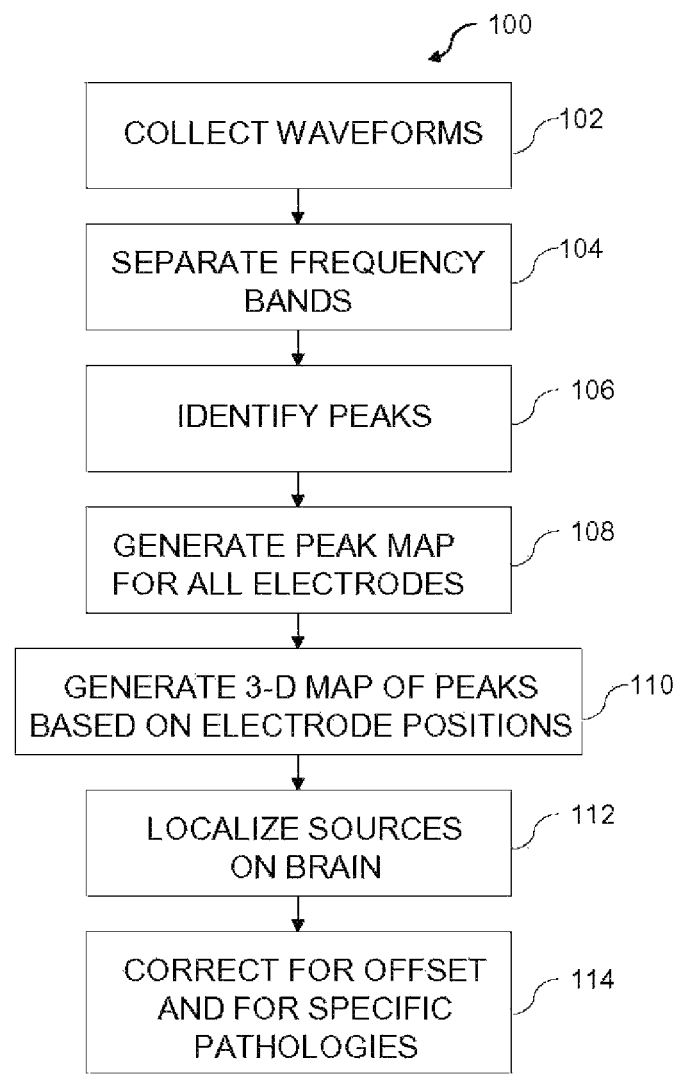
FIG. 5 is a flow chart diagram illustration of a possible method of source localization, in accordance with one embodiment of the present invention.
Figure 6:
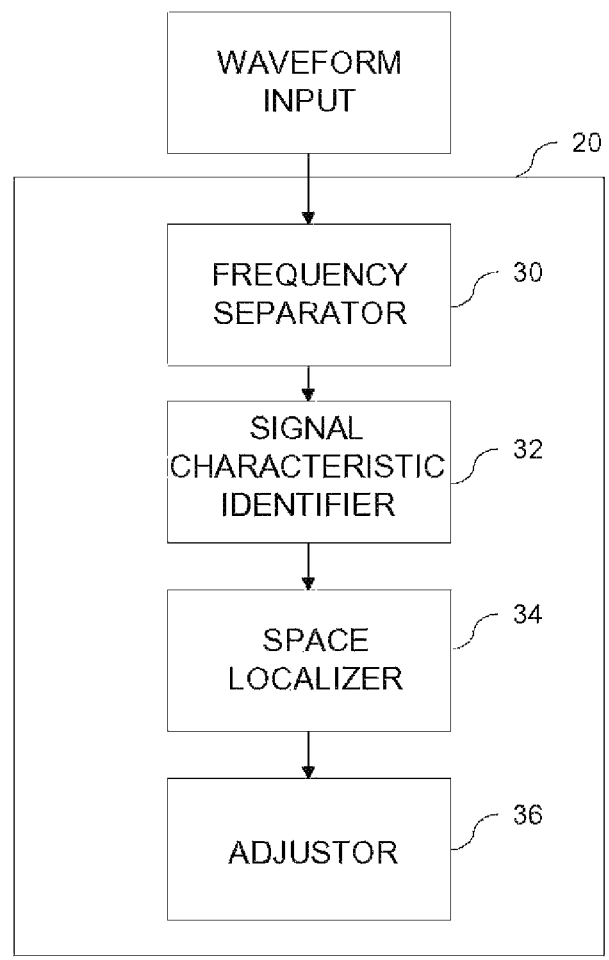
FIG. 6 is a block diagram illustration showing the components of a source localizer used in the method of FIG. 5.
Figure 7:
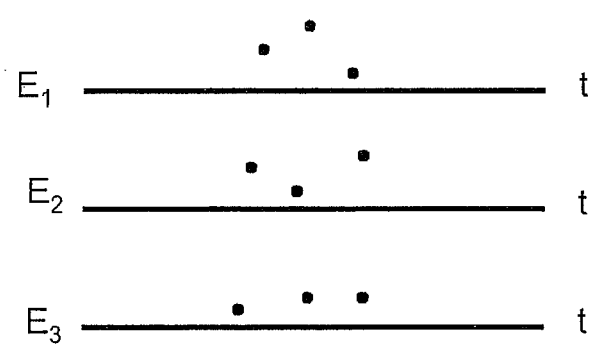
FIG. 7 is an illustration of a peak map for three electrodes.

Reference is now made to FIG. 5 and FIG. 6, taken together, where FIG. 5 is a flow chart diagram illustration of a possible method of source localization 100, in accordance with one embodiment of the present invention, and FIG. 6 is a block diagram illustration showing the components of source localizer 20, as used in the method of FIG. 5. Waveforms are collected (step 102) from either data collector 18 or from pattern generator 22, as described above. A frequency separator 30 can separate (step 104) frequency bands so as to make characteristics such as peaks of each waveform more readily identifiable. Alternatively, any other method, such as wavelet analysis, etc. could be used to separate superpositioned activity. Also any other wave characteristic could be used instead of peaks, such as wave envelope shape, etc. Signal characteristic identifier 32 then identifies (step 106) peaks, wavelets, or other discrete identifiable characteristics from the separated waveforms, and from the identified elements generates (step 108) a map for all of the electrodes 13, similar to the peak map shown in FIG. 7 for three electrodes. As shown in FIG. 7, each of electrodes $E_1 \ldots E_3$ has its own peaks each of which may be at a different strength. These peaks are identified and displayed in an array, such that it is possible to compare peaks on different electrodes for different points in time. It should further be noted that patterns may be identified from combined activities at different peaks. Furthermore, the combinations of synchronous activities at different frequencies may enable more precise description of the waveform, and may more closely relate to the actual neural pattern. Signal characteristic identifier 32, which in the present example is a peak map generator, uses the peak map to generate (step 110) a 3-D map of peaks based on the positioning of electrodes 13.

A space localizer 34 then uses the 3-D map of peaks to localize (step 112) the sources on the brain. It can offer alternative localizations to the pattern identified in the map of the scalp electrodes. Alternatively, source localization can be done by known methods such as low resolution electromotography (LORETA), for example. The localized activity is separated into discrete functional regions either "bottom-up" by patterning among subjects in the same experimental group, "top-down" on the basis of neuropsychological knowledge (i.e. Brodmann's division), or with a combination of both. It should be noted that, as was mentioned previously, localization may be improved via additional information about patterns from knowledge base 16.

Figure 8:
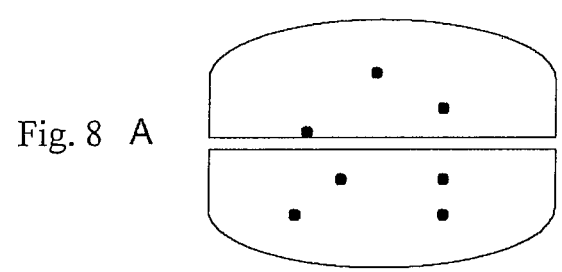
FIGS. 8A-8B is a schematic illustration of the brain as viewed from above having a first 3-D generated peak map (A) and a second 3-D generated peak map (B)
Figure 8:
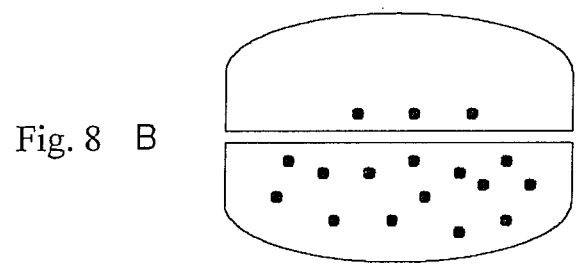

Finally, an adjustor 6 may correct (step 114) for any offsets and for specific pathologies that might result in skewed or missing elements from the pattern. For example, FIG. 8 is a schematic illustration of the brain as viewed from above having a first 3-D generated peak map (A) and a second 3-D generated peak map (B). For the purposes of description, it is to be assumed that both peak map A and peak map B were generated for the same activity in two different individuals. In peak map A, peaks are relatively evenly distributed, while in peak map B, there is a higher density on the lateral side. If both of these maps are compared to known maps in a database formed from many such trials, they can be corrected. This type of scenario may result from improperly placed electrodes, or from variations in head anatomy among subjects. Additionally, there may be some scenarios where a particular pathology destroys a portion of the brain. If there are missing peaks in a particular region that can be attributed to such a pathology (based on the database and possibly structural imaging input), corrections can be made for these situations as well.

Figure 9:
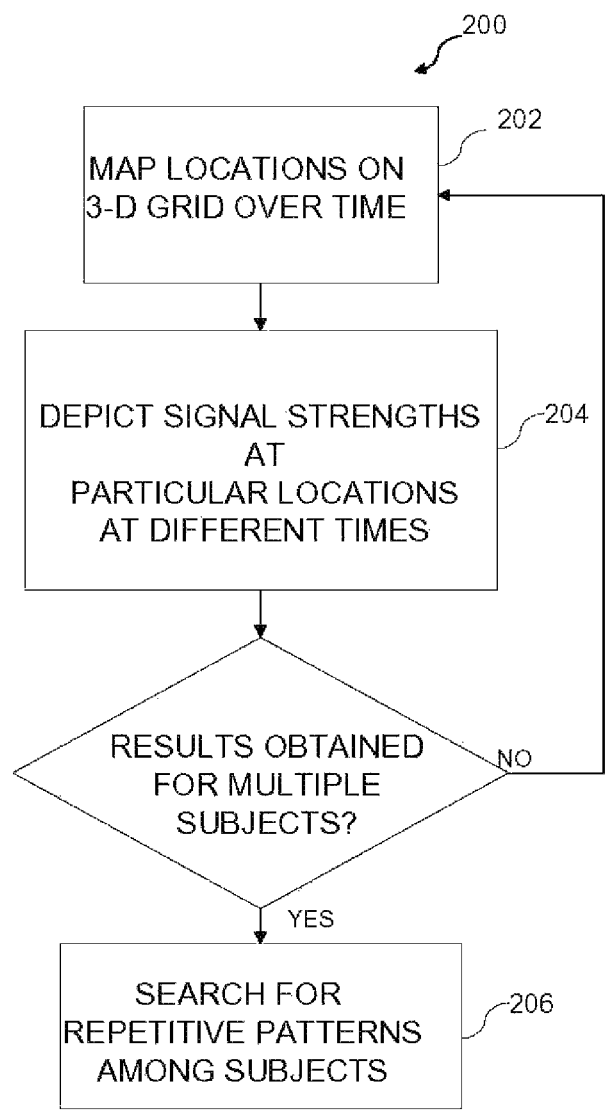
FIG. 9 is a flow chart diagram illustration of a method of pattern analysis, in accordance with a first embodiment of the present invention wherein source localization is performed prior to pattern analysis.
Figure 10A:
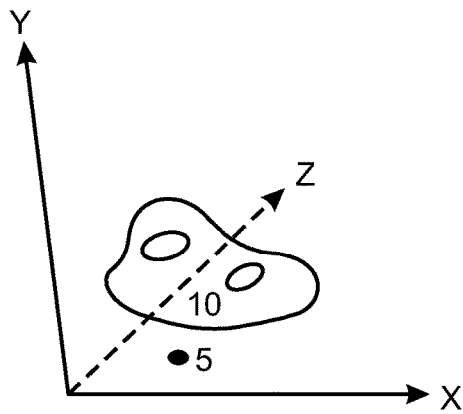
FIGS. 10A-10B are graphical illustrations of a step of the pattern analysis of FIG. 9.
Figure 10B:
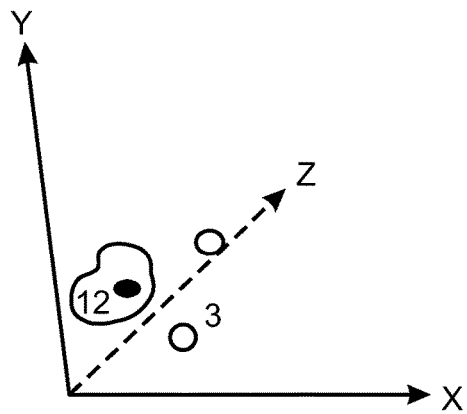

Reference is now made to FIGS. 9 and 10, taken together, where FIG. 9 is a flow chart diagram illustration of a method of pattern analysis 200, in accordance with a first embodiment of the present invention wherein source localization is performed prior to pattern analysis, and FIG. 10 is a graphical illustration of a step of pattern analysis 200, as will be described hereinbelow. First, locations found by source localizer 20 are mapped (step 202) onto 3-D grids over time. As shown in FIG. 10, at each time period, a different three-dimensional map of the various locations is generated, showing (step 204) signal strengths at locations for a primary time period A and a secondary time period B. Additional time periods may be included as well. Generally, the signal strengths and their spatial distributions change after a period of time (usually in the milliseconds—up to tens of milliseconds range). Thus, for example, at one time, particular localizations may demonstrate particular signal strengths (shown for example in FIG. 10 as strengths of 10 and 5 at two locations respectively), while at another time, other localizations may demonstrate different signal strengths (shown for example in FIG. 10 as strengths of 12 and 3 respectively). These steps are repeated for all of the subjects within the particular research group. Once patterns from multiple subjects are collected, pattern generator 22 searches for (step 206) repetitive patterns among subjects of the same research group. The patterns involve the timed activation of sets of regions, with temporal, spatial and strength tolerance. This is based upon counting the number of times a particular signal strength at specific spatial location (all, as stated, with tolerance) is obtained at a particular time period, pairs of such events, and so on to larger and larger groups of such events. Thus, a simple counting method is used to determine a pattern wherein patterns of activation of a set of regions, each with its strength/temporal/spatial characteristics that are repetitive among subjects of a certain research group, are identified—all within their dynamic tolerances. It should be readily apparent that the greater the number of inputs (i.e., the number of experimental subjects used), the more robust the pattern analysis will be.

Figure 12:
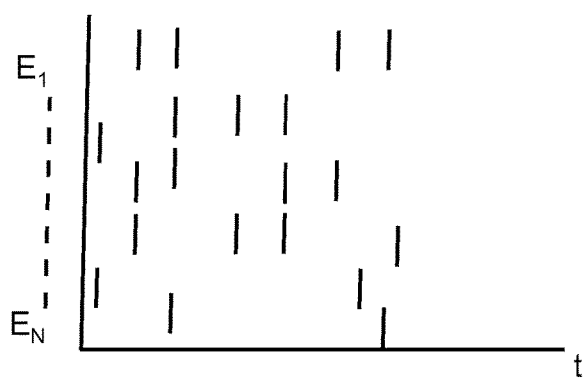
FIG. 12 is a graphical illustration of a raster plot, which serves as a basis of the pattern analysis of FIG. 11.
Figure 11:
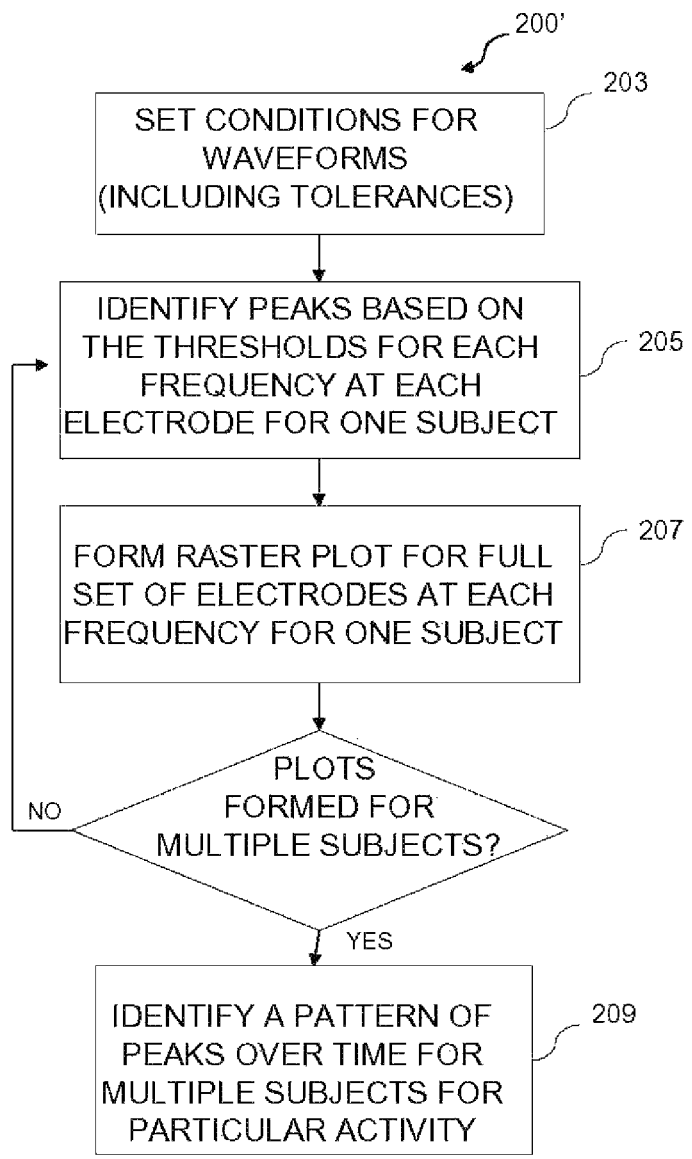
FIG. 11 is a flow chart diagram illustration of a method of pattern analysis, in accordance with another embodiment of the present invention wherein pattern analysis is performed prior to source localization.

Reference is now made to FIG. 11 and FIG. 12 taken together, where FIG. 11 is a flow chart diagram illustration of a method of pattern analysis 200', in accordance with another embodiment of the present invention wherein pattern analysis is performed prior to source localization, and is performed on waveforms directly obtained from electrodes 13, (or any other chosen characteristic of the sampled activity), and FIG. 12 is a graphical illustration of a raster plot, which serves as the basis of pattern analysis 200', as will be described hereinbelow.

First, pattern generator 22 sets (step 203) conditions (such as thresholds) for waveforms obtained from electrodes 13. In one embodiment, a binary type of threshold is used, wherein peak values above the threshold are included and values below the threshold are excluded. In another embodiment, a gradual scale may be included. As stated, not only peaks, but also wavelets, or other discrete identifiable elements for each electrode for the particular subject could be utilized. In one embodiment, waveforms which are of varying frequencies are separated out, and peaks are identified (step 205) for each frequency at each electrode for each subject. This step is repeated for all electrodes per subject. Next, pattern generator 22 forms (step 207) a raster plot for the full set of electrodes showing peaks over time. An example of a raster plot is depicted in FIG. 12. It should be noted that tolerances for time may be included as well, such that if the peak occurred within the determined tolerance it will be counted. It should further be noted that patterns may be identified from combined activities at different peaks. Furthermore, the combinations of synchronous activities at different frequencies may enable more precise description of the waveform, and may more closely relate to the actual neural pattern. These steps are repeated over multiple subjects and the results of the peak identification of multiple subjects over various frequencies over time are input into a processor which is configured to identify (step 209) a pattern of peaks over time for multiple subjects for a particular research group. Specifically, pattern generator 22 searches for repetitive patterns among subjects of the same research group. The patterns involve the timed activation of sets of electrodes, with temporal, spatial and strength tolerance. This is based upon counting the number of times a particular signal strength is obtained at a particular time period, pairs of such events, and so on to larger and larger groups of such events. Thus, a simple counting method is used to determine a pattern wherein patterns of activation of a set of electrodes, each with its strength/temporal/spatial characteristics that are repetitive among subjects of a certain research group, are identified—all within their dynamic tolerances. It should be readily apparent that the greater the number of inputs (i.e., the number of experimental subjects used), the more robust the pattern analysis will be. Those patterns are later used for comparison, as will be described further hereinbelow. The identified patterns are then sent to source localizer 20 for source localization.

Figure 13:
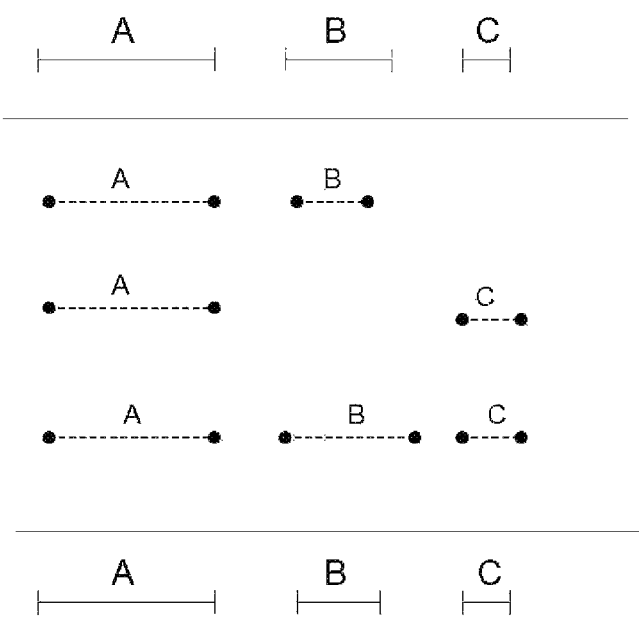
FIG. 13 is a schematic illustration of an example of identifying patterns comprised of a time-series of region activations including entailment relations among the regions.

Reference is now made to FIG. 13, which is a schematic illustration of an example of identifying patterns comprised of a time-series of region activations, but which also suggest entailment relations among those regions. This is based on the counting methods, in accordance with embodiments of the present invention. Although the following description refers to identified regions, as in the first embodiment of the present invention wherein source localization is done prior to pattern analysis, it should be readily apparent that similar methods may be used for identifying patterns based on electrode waveforms (or any other activity characteristic), as in the second described embodiment of pattern analysis. As shown in FIG. 13, and as described above with respect to pattern analysis, regions A, B and C are activated (at a certain strength, at a certain time) for the particular research group. However, not all regions become activated for all subjects, and timing may vary. Thus, the total number of times that any combination of the regions (for example, region A and B as shown in line 1 in FIG. 13) were activated at specific timing and with a specific strength for each research group are noted. The number of participating regions may be any number from one and up and each region can participate more than once without limitation at different times. In the current context, the word "entailment" is defined as a correlative relationship between two events, which may hint at causality. Thus, if event A entails event B, then event A correlates to event B and also might have a causal relationship with event B. Some initial conclusions as to the entailment relationships between region activations (for example, A entails B which entails C versus A entails both B and C independently) may be made. Those initial conclusions are based upon the relative timing among the participating regions. For example, in a first scenario, if one knows the relative timing of C after A over the different subjects in a research group (for example C occurs between t1 and t2 milliseconds after A) and then one looks at activations of C only after A together with B, if the relative timing period does not change significantly by including B, then B does not tend to contribute significant new information with regard to the timing of activation of C after A. On the other hand, in a second scenario, if the relative timing of C seems significantly related to B, then it does contribute new information. The first scenario is most likely indicative of an independent entailment of both B and C by A, while the second scenario is most likely indicative of a dependent one. It should be noted that by taking into account information from knowledge base 16, it is possible to improve the sensitivity and specificity of the patterns. In this way, a set of patterns is generated based on multiple subjects for each research group, and this pattern is then updated based on any new inputs or trials that are added later. Another way to achieve a similar result is via comparisons of spatial or strength relations among the regions (instead of temporal relations as presented here). This too will show whether there is additional dependent information or not.

Figure 14:
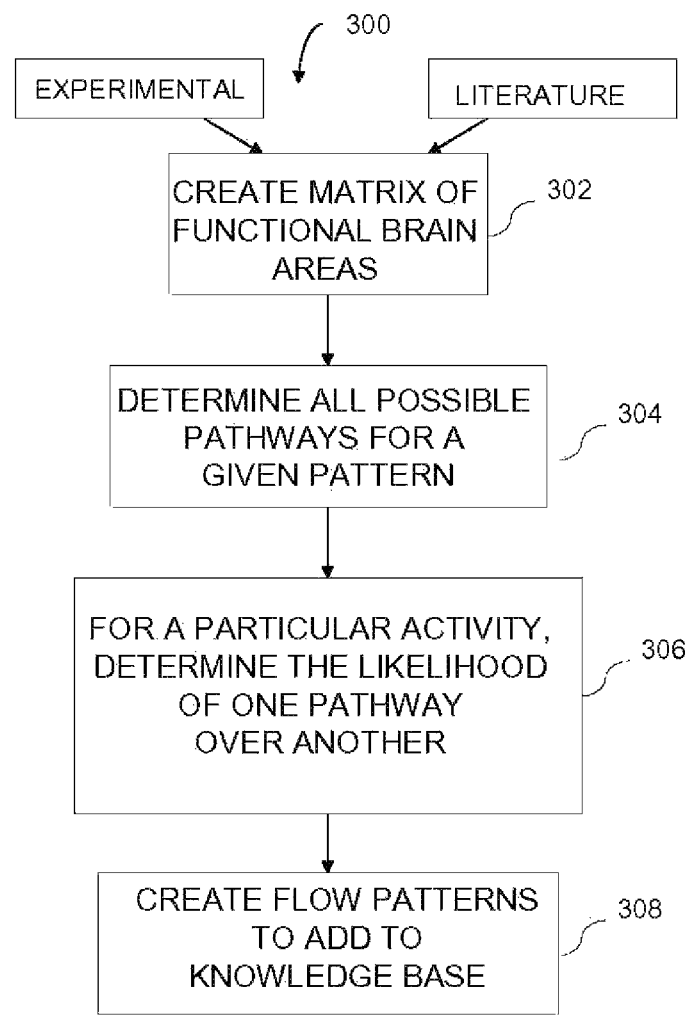
FIG. 14 is a flow chart illustration of a method of neuropsychological analysis, in accordance with embodiments of the present invention.

Reference is now made to FIG. 14, which is a flow chart illustration of a method of neuropsychological analysis (step 300), in accordance with embodiments of the present invention. The purpose of the neuropsychological analysis step (step 300) is enhancement of the patterns generated up until this point, as well as their interpretation into neuropsychological terms. Knowledge base 16 is used to help evaluate specific patterns identified by pattern generator 22, and based on the analysis to determine flow patterns including a sequence and duration of activated locations in the brain for each behavioral function and sub-function. These flow patterns are created for both the normal and pathological states, and knowledge base 16 including these flow patterns are accessible for comparison purposes for evaluating single subjects.

Neuropsychological analysis bridges bottom-up and top-down findings. The bottom-up input is a time-series of activities of functional regions which had been previously identified (in the pattern analysis phase) as being repetitive in at least one research group. The top-down input is the knowledge base including functional relations among brain regions. The output of the analysis is a description of possible neuropsychological flow patterns and translation of these flow patterns into neuropsychological terms. Automatic suggestions for correction when the comparisons are imperfect may be included in the output.

Figure 15:
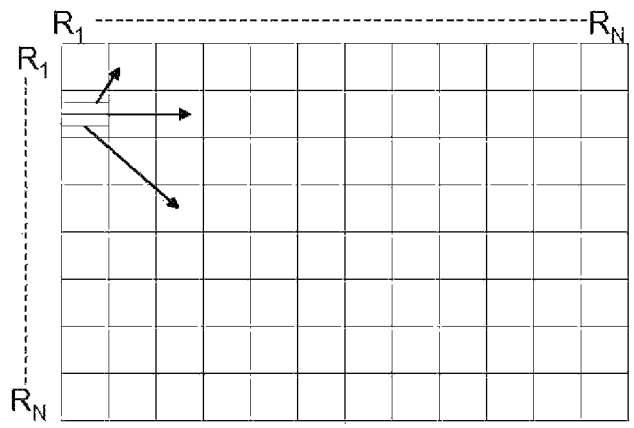
FIG. 15 is an illustration of a matrix representing regions of the brain.

In the top-down input, several levels of relationship indicators may be used to relate certain regions in the brain to others and thus to form a flow pattern. The first level may include a matrix or other representation of functional brain regions showing relationships between any two regions in the brain. The matrix is created (step 302) on the basis of new experimental data, produced in the manner described above or on the basis of data available in the literature, which provides scientific information regarding relationships of certain regions to other regions in particular behavioral functions. The data is rarely directly available in the literature in such a format and often must be deduced from the reports of activation of various specific regions in the specific behavioral function and in other functions and from knowledge regarding anatomical and functional relations among regions. Neuropsychological analyzer 24 retains an updateable database of these relationships, for example in matrix form. An example of a matrix is shown in FIG. 15, wherein regions $R_1 \ldots R_N$ of the brain are represented, down and across. Thus, each box represents a general functional region. Within each box, more specific subcategories of the region are distinguished from one another. As an example, if Region 2 represents vision as it relates to recognition of the human face, the particular subcategories might include, for example, familiar vs. unfamiliar faces. For a given behavioral function, each region may evoke activity in other regions. With rigorous analysis, information about functional relations among regions can be deduced to a degree from the neuropsychological and neurophysiological literature, and is further compiled by experimental methods such as the ones described in the present application. Thus, pre-existing knowledge about which regions are represented in what order for a particular state can help build the knowledge base, but actual data taken from the present system significantly aids in building the knowledge base, and the knowledge base is adjusted accordingly. It should be readily apparent that a matrix is only one way of depicting flow patterns, but other representations are possible as well. As shown in FIG. 15 and stated above, one subcategory may be generally known to lead to a particular region, while another subcategory from the same source region is known to lead to a different region. This information can help in determination of a flow pattern for specific behavioral functions and particularly for sub-functions. Flow patterns can be determined for common sub-functions such as, for example, inhibition, working memory, attention, etc. Alternatively, flow patterns can be determined for particular higher order behavioral functions. The preference among the patterns in the knowledge-base, when comparing them with the patterns from the analysis of previous stages as described above is: (1) patterns for the precise behavioral function at hand, (2) patterns to sub-functions, which are expected in the behavioral function at hand, and (3) patterns which are based upon the functional relations between regions (as in the matrix format).

Figure 16:
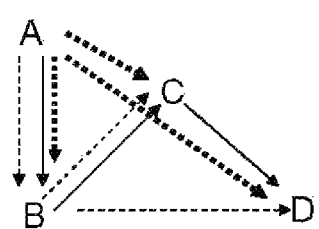
FIG. 16 is a schematic representation of different flow patterns for identified regions, wherein each of the flow patterns is expected to have different neuropsychological meaning.

Returning now to the flow-chart illustration of FIG. 14, the above three components, in their preferred order, are used to determine (step 304) all possible flow patterns for a given time-series of region activities. For example, as shown in reference to FIG. 16, there may be many different flow patterns involving the identified regions at their specific times of activation, and each pattern is expected to have different neuropsychological meaning. As shown in FIG. 16 as an example, if the regions identified are regions A, B, C and D, one possible pathway would be A leads to B which leads to C which leads to D, as shown with solid arrows. Another possibility might be that A leads to B, C and D all together, as shown with short dotted arrows. Yet another possibility might be that A leads to B, and B leads to C and D together, as shown with long dotted arrows. Each of these possibilities might underlie quite a different neuropsychological process. For example, an auditory sensation might activate association in a higher representation area (for example of a voice of a friend), which then in turn might activate association of emotional significance. Alternatively, an activation of another auditory sensation, such as the roar of a tiger might activate by itself the emotional significance representation at its relevant regions and also activate independently the higher representation area. Thus the arrangement of flow among the same regions will have quite a different neuropsychological meaning. Once all possible pathways have been determined, the likelihood of it being one pathway over another is calculated (step 306) for the particular behavioral function. This likelihood is based as stated on the three components of the knowledge-base as described above, and is then used to help create (step 308) flow patterns and to build the knowledge base 16. Automatic suggestions for correction when the comparison to known flow patterns is imperfect may be included in the output.

The flow of the algorithm for comparing obtained patterns to the patterns in the knowledge base and for translating the obtained patterns into neuropsychological terms can be as follows. First, on the basis of the pair level comparison (matrix as described above), the time-series is scanned, and all possible relations among regions are marked. The matrix may also include temporal constraints (for example, region A can activate region B at a certain temporal delay with tolerance). Those delays are then imposed in the scan. The output of this stage is either a graph, which is composed of all the possible relations among regions, or a set of isolated sub-graphs, each composed of all the possible relations among its regions. The sub-graphs are separated from one another, because there is no legitimate relation between at least one region in one sub-graph and one region in the other sub-graph. For each sub-graph (or if there is one graph, for the entire graph) all possible combinations of relations (depicted, for example, as arches) which would still span the graph are computed. For example, if a sub-graph is composed of regions A, B and C and it is known from the matrix that at the relevant temporal delays, A can activate B, A can activate C and B can activate C, the possible combinations for the sub-graph would be: (1) A activates B, which activates C; (2) A activates both B and C; and (3) A activates both B and C and the activation of B further activates C. All possible combinations are thus described and counted.

A general grade of the match between the bottom-up and the top-down findings is given based on the number of sub-graphs. The less comprehensive the graph (the more sub-graphs there are) the lower the grade.

An automatic search is evoked to suggest improvements to the results, so that the graph is more comprehensive. This means that the relations between each 2 sub-graphs are scanned to find possible manners to combine them at a minimal cost, as will be hereby described.

The minimal cost corrections could be either via suggestions of correction to the bottom-up process, to the top-down process or both. They are based on the ability to replace a certain region in one (or more) of the sub-graphs, to remove it, or to add a new region. This ability is based on specific considerations, as follows. In correction of the source localization component and with regard to the nature of source localization algorithm employed, the improvement is in finding alternative regions which may have been active and which would connect the sub-graphs. For example, often neighboring regions, which are included, are likely to be erroneously excluded. The analysis is based in this case on the anatomical distance between regions. That is, for example, if a region could be added/replaced which is directly a neighbor of an existing region, it may have a cost of 1; if there is an additional region between them, it may have a cost of 2, etc. Thus, a scan is performed for minimal cost of anatomical distances of additions/replacements/deletions which combines the sub-graphs in accordance to known features of the localization algorithm.

In correction of the pattern analysis component and with regard to the nature of the pattern recognition algorithm employed, a similar scan would look for regions that may have been just out of the tolerance ranges (or alternatively for deletion just within tolerance ranges) or just below (or alternatively for deletion just above) threshold and which enable connecting the sub-graphs. Here the cost is based on deviation from thresholds and tolerance margins.

In correction of the knowledge-base, it is known that if region A tends to activate region B, which tends to activate region C, then to a lesser degree region A will often directly activate region C. A correction is thus based on adding such "jumps" and the cost is the "jump" distance. Once the knowledge base grows and as it is directly linked to published references, another correction is to point out published references which have shown relations currently excluded from the knowledgebase, or alternatively to point out published references which state that a currently included relation is incorrect. The number of relevant references and their scientific significance (impact factor, etc.) are evaluated as the basis for cost in this case.

The sub-graph combinations may also be ranked. The ranking is based on the hereby described preference. Sub-graph combinations which involve paths that are task-related for the relevant task employed are highly ranked. Paths which relate to general sub-functions also gain rank scores (it is possible that more than one sub-function will be found and the rank gains can be combined accordingly). The basic rank is for pair-level relations. Any of those three levels also have inter-level preference rank. Thus, all in all, each sub-graph combination is ranked according to likelihood as well.

Finally, according to the translation component of the knowledgebase, each graph, either corrected or basic, is translated into neuropsychological terms. The translation is also based upon the three components—namely task-specific flow patterns, behavioral sub-function flow patterns and pair level.

Figure 17A:
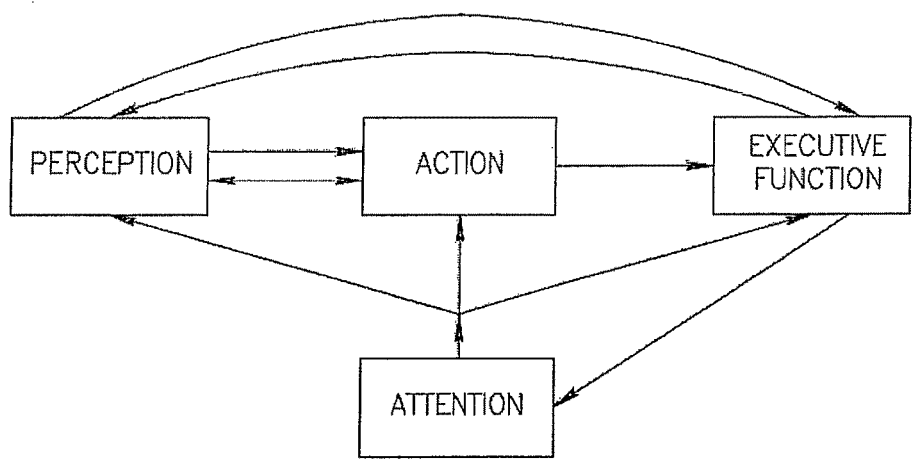
FIGS. 17A-17E are schematic illustrations of flow patterns showing connectivity between functional regions.
Figure 17B:
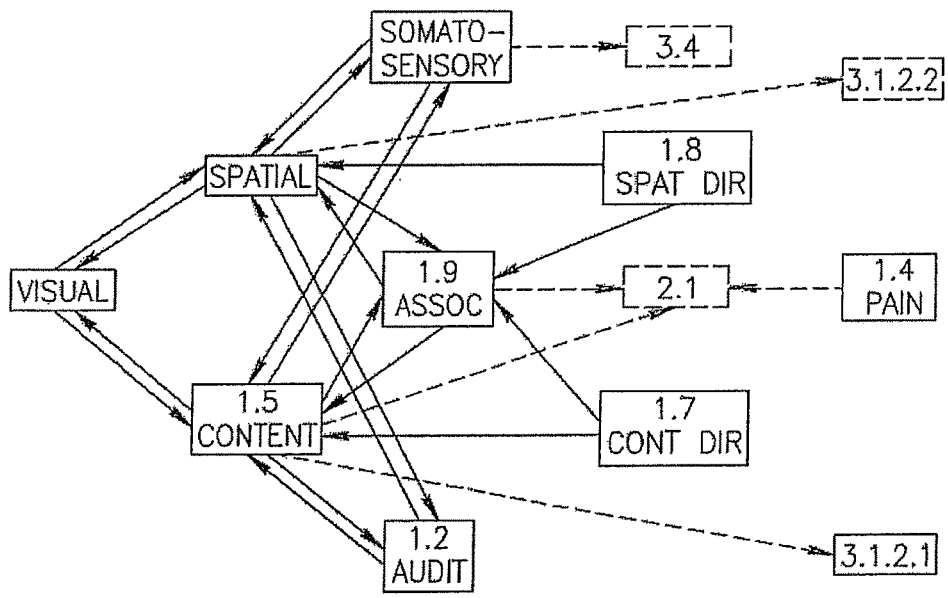
Figure 17C:
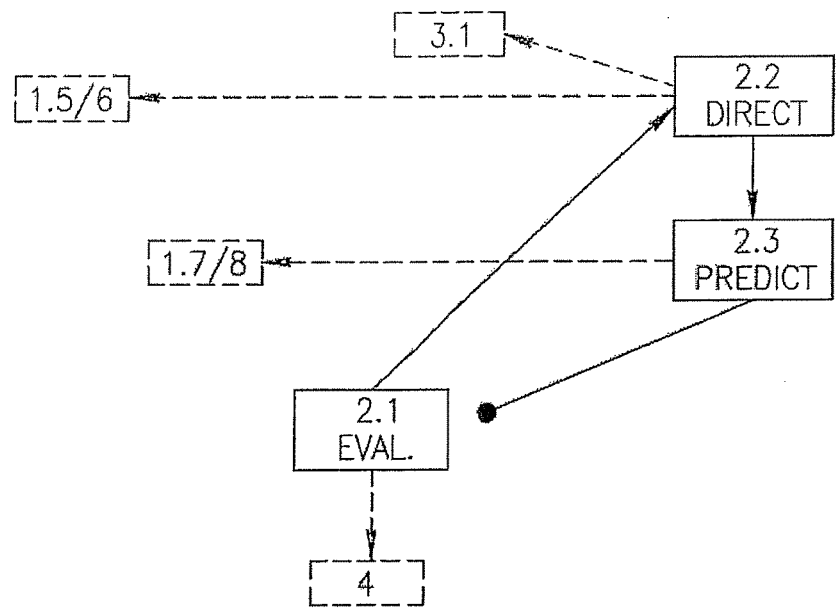
Figure 17D:
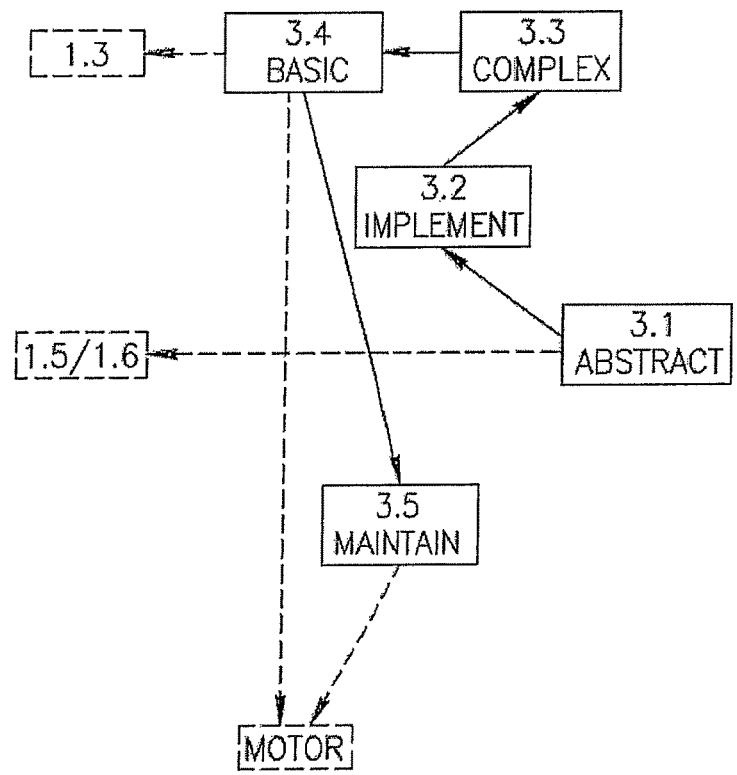
Figure 17E:
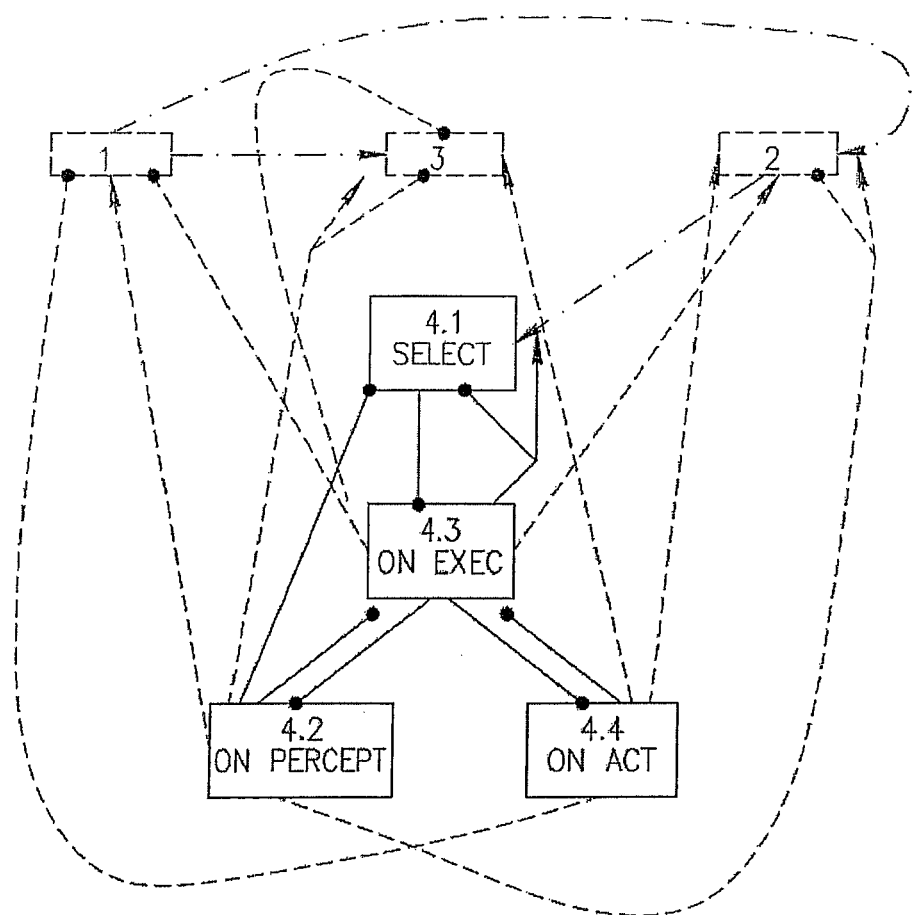

Several examples of flow patterns showing connectivity between functional regions is shown in FIGS. 17A-17E and associated Table 1 which relates functional regions to the numbering on the figures. These diagrams were formed based on published literature. It should be readily apparent that these are merely examples, and do not necessarily represent actual patterns. Moreover, many alternatives may be suggested based on theory and experimental findings. FIG. 17A is a diagrammatic representation of global inter-relationships between an action, perception, executive function and attention. FIGS. 17B-17E are more specific diagrammatic representations of perception, executive function, action and attention, showing relationships and interrelationships between different areas of the brain which are functional during these activities. Similar models may be created for particular tasks, behaviors or activities, as described with respect to the present invention.

TABLE 1

| Modules | | | |
|---|---|---|---|
| Functional module | Hemi | BA | Neuroanatomy |
| 1. Perception | | | |
| 1.1. Visual | | | |
| 1.1.1. Primary visual | X | 17 | |
| 1.1.2. Secondary visual | X | 18 | |
| 1.1.3. Tertiary visual | | | |
| 1.1.3.1. Objective oriented | Lt | 19 | |
| 1.1.3.2. Subjective oriented | Rt | " | |
| 1.2. Auditory | | | |
| 1.2.1. Primary auditory | Bi | 41 | |
| 1.2.2. Secondary auditory | Bi | 42 | |
| 1.2.3. Tertiary auditory | | | |
| 1.2.3.1. Objective oriented | Lt | 21, 22 | |
| 1.2.3.2. Subjective oriented | Rt | " | |
| 1.3. Somatosensory | | | |
| 1.3.1. Primary somatosensory | X | 1, 2, 3 | |
| 1.3.2 Secondary somatosensory | X | | Parietal operculum |
| 1.4. Pain | | | |
| 1.4.1. Primary pain | X | | Posterior Insula |
| 1.4.2. Secondary pain | | | |
| 1.4.2.1. Objective oriented | Lt | | Anterior Insula |
| 1.4.2.2. Subjective oriented | Rt | | " |
| 1.5. Heteromodal content | | | |
| (a) Objective oriented | Lt | | |
| (b) Subjective oriented | Rt | | |
| 1.5.1. Visual-Auditory | | 37, 20 | |
| 1.5.2. Visual-Somatic | | 39 | |
| 1.5.3. Global | | 38 | |
| 1.6. Heteromodal spatial | | | |
| 1.6.1. Body | X + Rt | | Superior parietal lobule |
| 1.6.2. Milieu | X + Rt | | Inferior parietal lobule |
| 1.7. Short term content direction | | | |
| 1.7.1. Objective oriented | Lt | | Ventral posterior cingulum |
| 1.7.2. Subjective oriented | Rt | | Ventral posterior cingulum |
| 1.8. Short term spatial direction | X | | Dorsal posterior cingulum |
| 1.9. Association | | | |
| 1.9.1. Objective oriented | Lt | | Hippocamus + parahippocampal |
| 1.9.2. Subjective oriented | Rt | | Hippocamus + parahippocampal |

TABLE 1-continued

Modules

| Functional module | Hemi | BA | Neuroanatomy |
|---|---|---|---|
| 2. Executive function | | | |
| 2.1. Significance evaluation | | | |
| 2.1.1. Objective oriented | Lt | | Amygdala |
| 2.1.2. Subjective oriented | Rt | | " |
| 2.2. Executive direction | | | |
| (a) Content direction | LT | | |
| (b) Spatial direction | RT | | |
| 2.2.1. Top level | | 9, 10 | |
| 2.2.2. Basic level | | 46, 47 | |
| 2.3. Outcome prediction | | | |
| 2.1.1. Objective oriented | Lt | | Ventromesial prefrontal cortex |
| 2.1.2. Subjective oriented | Rt | | Ventromesial prefrontal cortex |
| 3. Action | | | |
| 3.1. Abstract action | | | |
| 3.1.1. Content action | Lt | 44, 45 | |
| 3.1.2. Spatial action | Rt | " | |
| 3.2. Implementation | X | | Medial cingulum |
| 3.3. Complex action | | | |
| 3.3.1. Body | X | 6 | |
| 3.3.2. Eyes | X | 8 | |
| 3.4. Basic action | X | 4 | |
| 3.5. Action maintenance | II | | Cerebellum |
| 4. Attention | | | |
| 4.1. Process selection | | | |
| 4.1.1. Executive selection | | | |
| 4.1.1.1. Content selection | Lt | | Ventral basal ganglia |
| 4.1.1.2. Spatial selection | Rt | | " |
| 4.1.2. Implementation selection | X | | Dorsal basal ganglia |
| 4.2. Perceptual attention | U | | Locus Ceruleus |
| 4.3. Executive attention | U | | Ventral tegmental area |
| 4.4. Action attention | U | | Raphe nuclei |

A method of pattern recognition in accordance with additional embodiments of the present invention is now described.

DEFINITIONS

Entity—either (1) a basic symbol in the input order series, which is, in the current application, an active functional area, or (2) a pair as it is defined below. The first entities are basic symbols and as the algorithm runs, new entities are formed, which can be composed of 2 basic symbols, and then of a basic symbol and a previous pair, 2 previous pairs and so on.

Occurrence—a specific event of an entity in the order series. Each entity, whether basic or complex, can occur in many entries. As will be presented below, an occurrence of a complex entity can spread over more than one entry. As a means of convection, complex entities will be considered as occurring in the first entry they involve. As will be presented below, they will include the necessary information regarding the other entries involved in them.

Pair—a relation between 2 entities. The pair could be built of entities in the same order entry, or of entities from different order entries—for example with a delta of 1 entry, 2 entries etc. Thus, the definition of each pair involves also the delta between the order entries. If the 2 entities are of the same entry, the delta is 0. Thus the pair (i,j|0) means a relation between entity i and between entity j in the same entry; the pair (i,j|1) means a relation between entity i and entity j in a consecutive entry; the pair (j,i|1) means a relation between entity j and entity i in a consecutive entry. Note that pair (j,i|0) is the same as pair (i,j|0) because at the same entry, there is no order difference.

Ancestor entities—defined for complex entities, composed of at least one pair, these are the entities which are paired with other ancestor entities at any step in the process of creating the complex entity. For example, suppose entities i & j were paired as (i,j|0) and then paired with entity k as ((i,j|0),k|0). Suppose also that entities l & m were paired as (l,m|0). Now suppose that both complex entities were paired as (((i,j|0),k|0),(l,m|0)|0). Let us term this new entity—x. The ancestor entities of x are then: 1. ((i,j|0),k|0), 2. (l,m|0), 3. (i,j|0), 4. k; 5. l, 6. m, 7. i & 8. j.

Independent pair—a pair that reflects a relation which does not result from other pairs.

Dependent pair—a pair that reflects a relation which results from other pairs. For example, if i, j and k are entities, which hold the following relations: i→j→k, then (i,j|$\Delta_{ij}$) and (j,k|$\Delta_{jk}$) are independent pairs, while (i,k|$\Delta_{ij}+\Delta_{jk}$) is a dependent pair. Statistical significance of a pair (i,j|$\Delta_{ij}$)—If entity i occurs $x_i$ times in an order series, which includes n entries altogether, and entity j occurs $x_j$ times in the same order series, then the probability of occurrence of entity i is $x_i/n$ and the probability of occurrence of entity j is $x_j/n$. The probability of random co-occurrence of entity i & j, with any $\Delta_{ij}$, in the same order series entries, $p_{ij}$ is the product of $(x_i/n)$ & $(x_j/n)$. This is provided that $\Delta_{ij}$ is small enough when compared to n and neglecting near edge distortions, by which occurrences of i in the last $\Delta_{ij}$ entries of the order series could not be followed by j. If the real co-occurrence of entities i & j, with a specific $\Delta_{ij}$, in the same order series entry is $x_{ij\Delta ij}$, it is possible to use the binomial distribution to evaluate the statistical likelihood of it. The formula of the binomial distribution is $$F(x, p, n) = \sum_{i=0}^{x} \binom{n}{i}(p)^i(1-p)^{(n-i)}$$

in our case: x is $x_{ij\Delta ij}$, p is $p_{ij}$ and n is n. The value computed denotes the likelihood that $x_{ij}$ co-occurrences will occur randomly. The smaller this value the greater the likelihood that the event is not random. We use an arbitrary threshold of 0.001 to define significant pairs. Note that both independent and dependent entities can be significant.

The goal of this method of pattern analysis is to start from the order series data and to expose the activity relations structure, or the relation patterns. As an example, suppose the symbols in a given dataset are i,j & k. The activity relation patterns, or the activity relations structure, in the dataset are precisely the following: symbol i entails symbol k in the same order entry, with a likelihood of 0.5, and symbol i together with symbol j in the same order entry entail symbol k in the following order entry, with a likelihood of 0.75. Furthermore, suppose that symbol i and symbol j occur spontaneously with a random likelihood of 0.4 and 0.8 correspondingly and symbol k does not occur spontaneously. This relations structure might lead to the following order series:

|  | Entry | | | | | | | |
|---|---|---|---|---|---|---|---|---|
| Symbol | 1 | 2 | 3 | 4 | 5 | 6 | 7 | 8 |
| i: | ACTIVE |  | ACTIVE |  |  | ACTIVE |  | ACTIVE |
| j: | ACTIVE | ACTIVE | ACTIVE |  | ACTIVE |  | ACTIVE | ACTIVE |
| k: |  | ACTIVE |  | ACTIVE |  | ACTIVE |  |  |

While the current algorithm presented is aimed for an order series data, the theoretical principles of the algorithm, which will be explained below, would be applicable to a time series, which basically involves tolerance in the precise timing among related occurrences of entities. Furthermore, while the current activity analyzed is in terms of active/inactive, the theoretical principles are also applicable to a scale of possible values for the occurrences of an entity, which would require strength tolerance. Note that, as is evident from the example above, in a finite dataset, there could be various possible data structures. It is possible to add a possibility to form all alternatively plausible relation structures for a given dataset along with rankings of likelihood.

Figure 18:
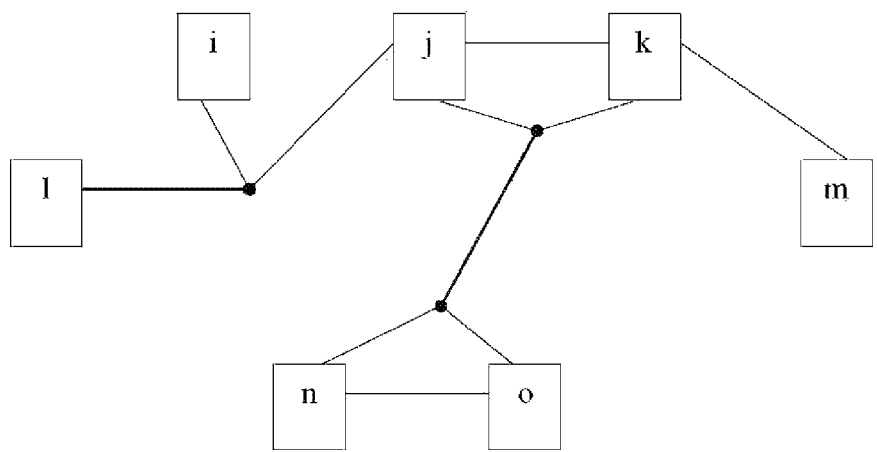
FIG. 18 is a schematic illustration of a relation structure.

A relation structure is divisible into pairs and simple groups. Reference is now made to FIG. 18, which is a schematic illustration of a relation structure. Each relation has its own strength of significance and temporal delta. Furthermore, if the temporal delta is more than 0, the relation also has temporal direction. However, for the purpose of the current point, it is possible to ignore those characteristics. A relation structure is composed of pairs of entities and of simple groups of entities. The pairs are evident in the presented structure—for example, (j,k); (k,m); (j+k,n+o); etc. A simple group is composed of entities, which tend to occur together. For example in the presented structure, the node uniting i, j & l marks a group. Note that j,k & m are also connected and in a sense occur together, but this results from the pairs (j,k) and (k,m) which happen to co-occur. On the other hand, the entities comprising a simple group, or in the example, the entities i,j & l, occur together significantly beyond random co-occurrence of the various pairs composing it. In terms of dependent probabilities, in the trio j, k & m, if it is known that k occurred, knowing further that j occurred as well, does not increase the likelihood for m to occur. However, in the trio i, j & l, knowing that any entity occurred together with any other entity increases the likelihood of the $3^{rd}$ entity to occur. The dependent probability considerations are extendable to simple groups larger than trios in a straightforward manner.

More complex structures are also divisible into pairs and simple groups. Already the structure presented involves a pair composed of prior pairs ((j,k),(n,m)). More complex relations are also divisible in a similar manner to pairs and simple groups. Note that multiple relations among basic symbols or complex entities are also possible. For example, in the above structure, entities i & l could have been also paired directly in addition to the group they form with j. Nevertheless, this additional relation is still a pair. Also note that a negative relation between entities, complex or basic, is also possible. A negative relation means that the involved entities tend to co-occur significantly less than what would have been expected randomly. Or in other terms, if one of those entities or group of entities occurs, the likelihood of the other entailed entity or group of entities to co-occur reduces significantly. Again a negative relation is still a pair or a simple group relation.

Thus, it is possible to divide relation structures to pairs of entities and simple groups, down to the level of basic symbols. Furthermore, note that each simple group could be described in terms of pairs, where at first 2 entities are paired to form the core pair of the group, then this core pair is paired with another entity to form the core trio and so on. Thus, it is possible to divide any relations structure consistently to 2 parts, down to the level of the basic symbols. This, however, means that for a given order series dataset, it is possible to expose the underlying relations structure on the basis of pairing from the basic symbols upwards. It is only necessary to pair correctly the algorithm presented here. Choice of threshold, sample size and method for calculating statistical significance will all determine sensitivity and/or specificity of the method.

In order to maximize correct results, strongest relation pairs are included as new entities. Therefore it should be noted that if there are 2 independent relations—for example (i,j) and (j,k) which underlie to a dependent relation (i,k), the 2 independent relations are always stronger then the dependent one. This is because the dependent relation is a mere random co-occurrence of the independent relations and its probability is the product of the probabilities of the independent relations and therefore it is smaller. Thus, if pairs are selected in the algorithm's ordered pairing process, it means they are independent. We further reduce from the dependent pair count the occurrences which result from the co-occurrence of the 2 independent pairs and thus, if the dependent pair does not occur significantly beyond those occurrences, it will be excluded as insignificant. It will be included only as dependent by later unification of the 2 independent relations. Note that if it occurs significantly also independently beyond those occurrences, it is selected as independent and regains all the reduced occurrences. Lastly, as will be described in the below, for each newly selected pair, its relations with the other entities are computed. If this new pair (i,j) relates strongly with the entity k, it will form a simple group ((i,j),k). However, if k relates more strongly to one of the pair's comprising entities, it will relate to it and the 2 pairs could later be united—for example, ((i,j),(j,k)).

Figure 19:
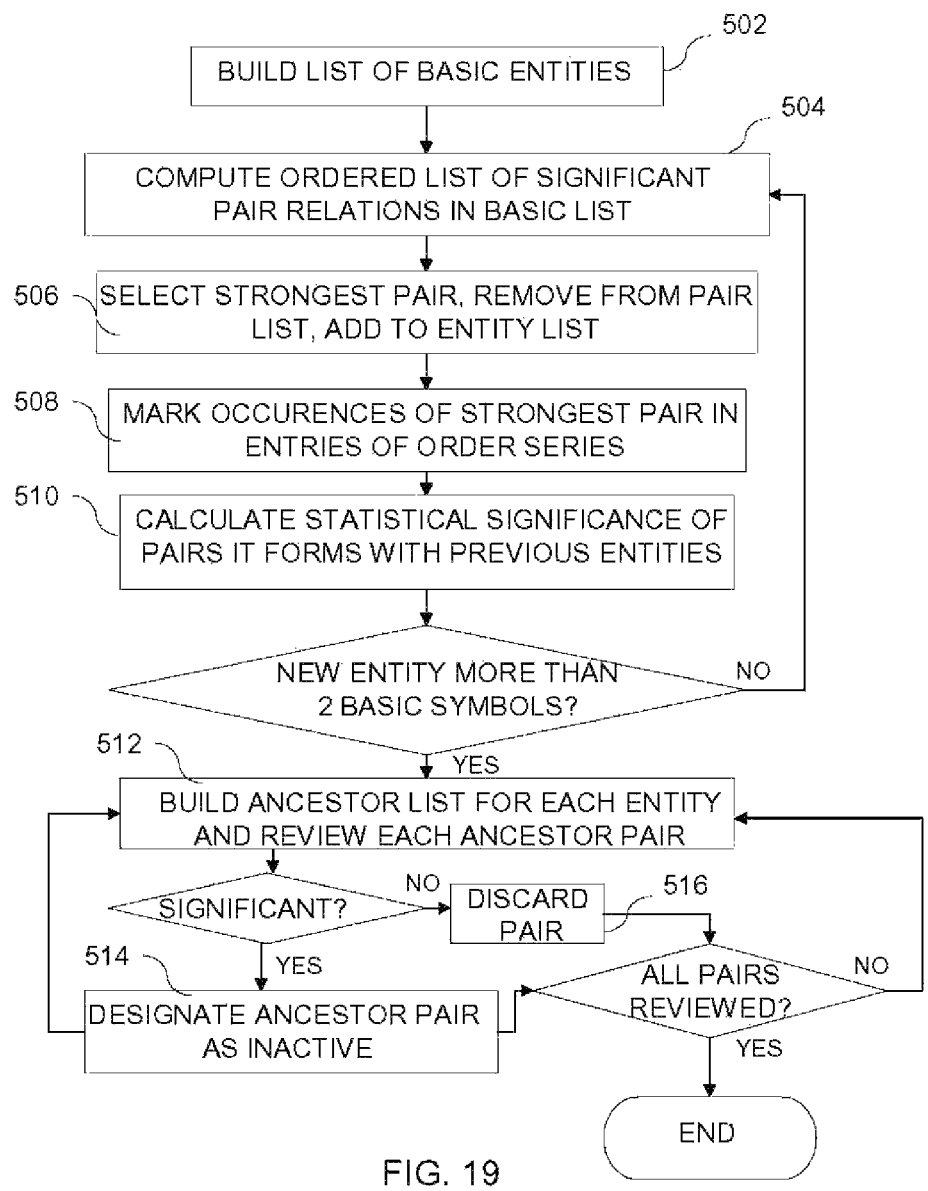
FIG. 19 is a flow-chart illustration of a method of pattern analysis.
Figure 20A:
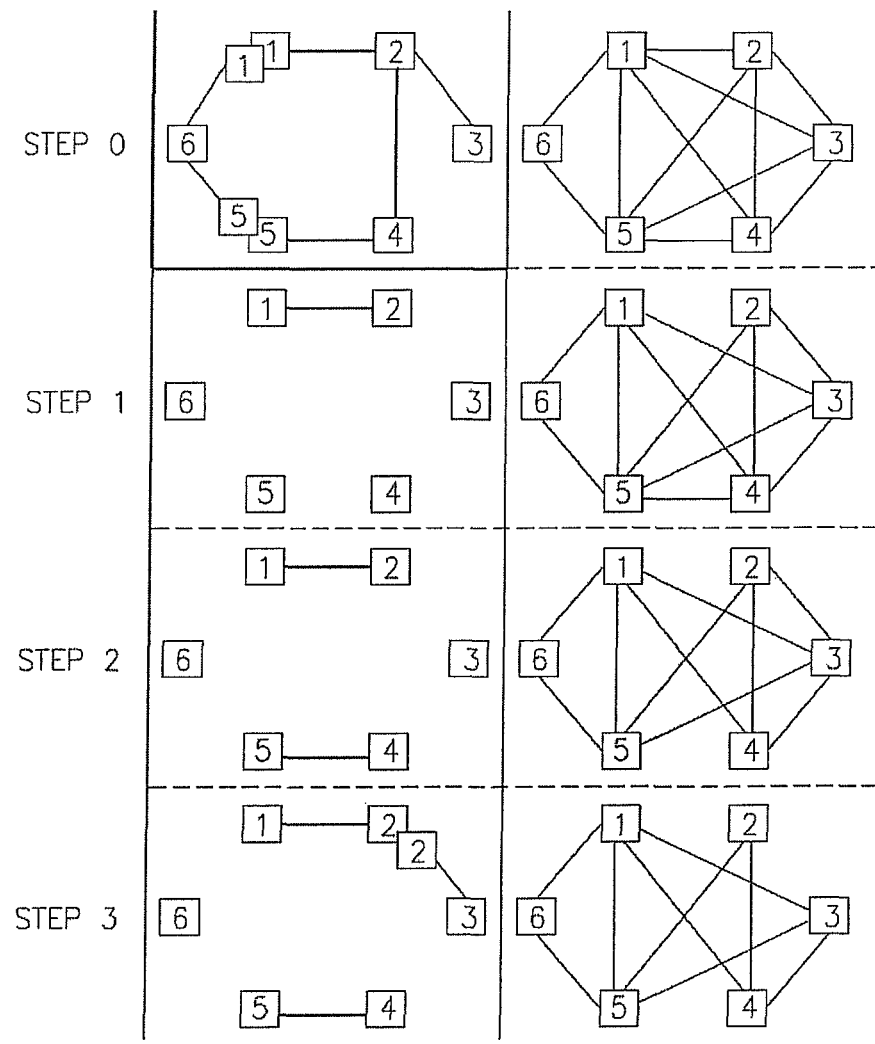
FIGS. 20A-20C are schematic representations of the method of FIG. 19.
Figure 20B:
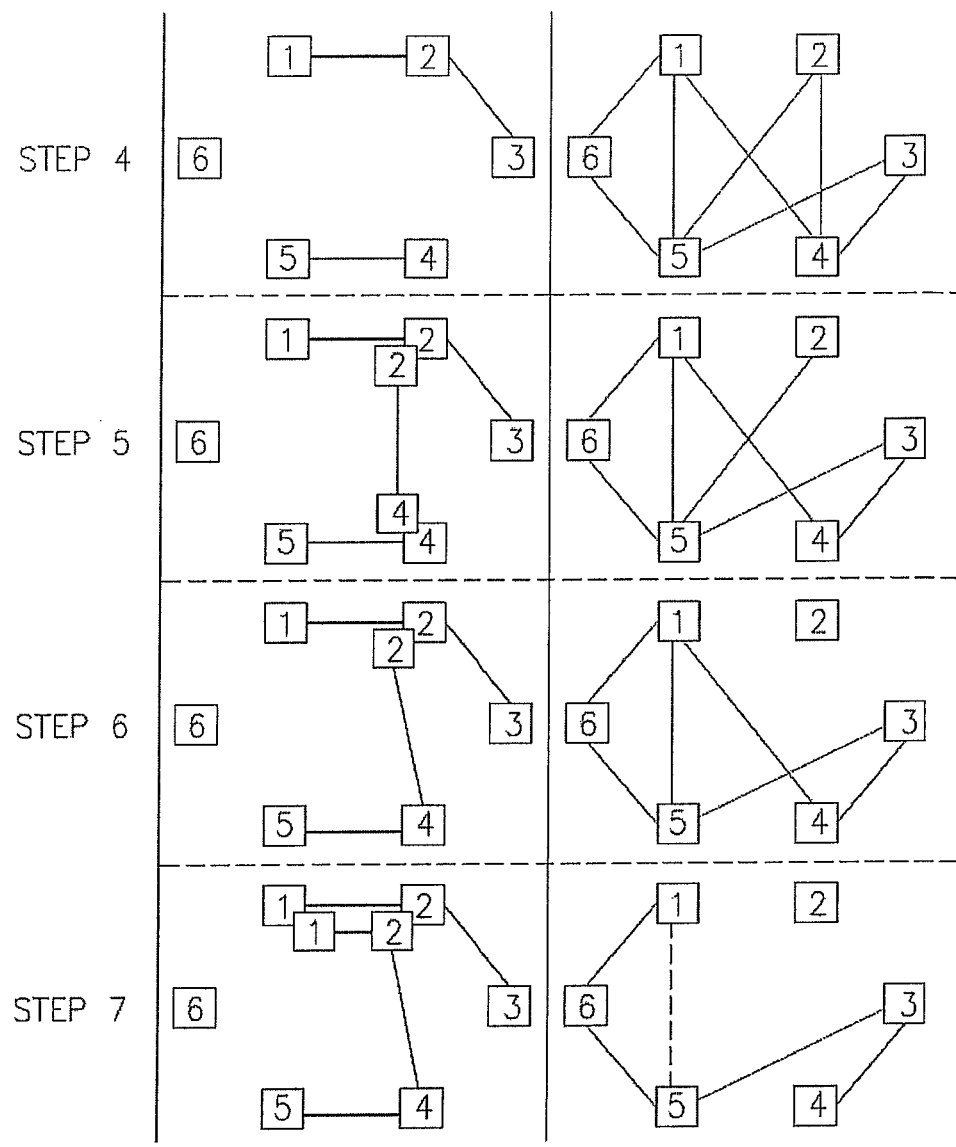
Figure 20C:
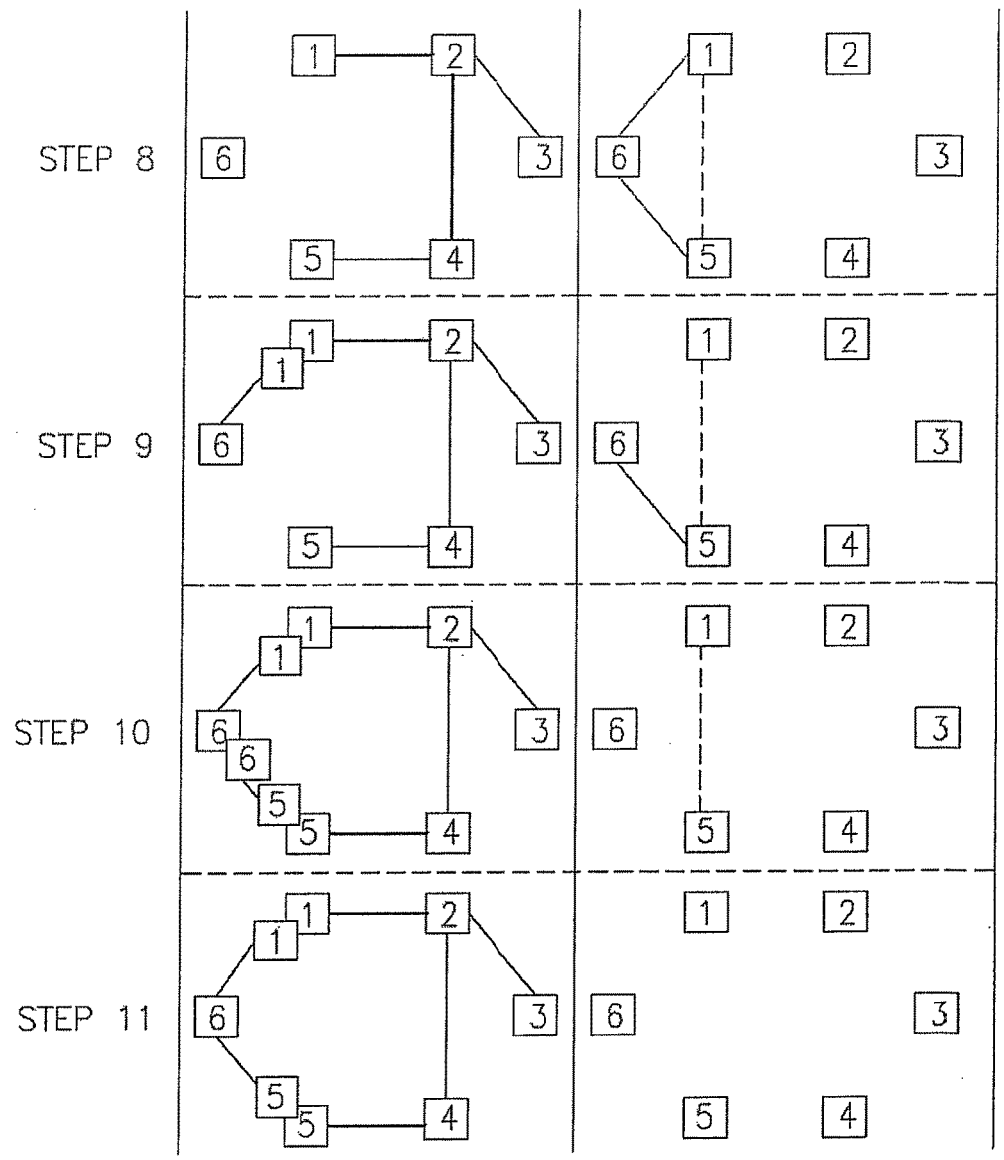

Reference is now made to FIG. 19, which is a flow-chart illustration of a method of pattern analysis, and to FIGS. 20A-20C, which is a schematic representation of the method of FIG. 19. First, a basic list of entities is built (step 502). This list of entities is a list of basic symbols. Next, an ordered list of all significant pair relations between various entities in the basic list is computed (step 504). As defined above, pairs could involve either entities from the same entry or entities from different entries, with a certain delta between them. The list is ordered, so that the most significant pair comes first, followed by the second strongest and so on. Note that only significant pairs, below the significance threshold, are included in the list. Next, the strongest pair is selected (step 506) from the top of the list, and added to the entities' list as a new entity. It is also removed from the significant pairs list. Next, occurrences of the strongest pair in the relevant entries of the order series are marked (step 508). This marking also includes occurrences which might have been previously designated inactive. This is because once a pair is selected, it is allowed to pair with other entities even in occurrences where it is a merely a subset of previously discovered entities. Next, the statistical significance of the pairs it forms with other previous entities is calculated (step 510) according to their co-occurrence in the order series. Next, if the new entity is more than a pair of two basic symbols (ie, includes at least one previous pair), then a first ancestors list and a second ancestors list are built (step 512). The first ancestors list includes all of the entities which are ancestors to the first entity of the new pair. The second ancestors list includes all of the entities which are ancestors to the second entity of the new pair. All pairs of entities from the first and second ancestors lists are reviewed. For each ancestor pair, if the pair is in the significant pairs list, then the order series is reviewed and for every entry which includes an occurrence of the new entity, the ancestors pair is designated (step 514) as inactive. Note that it may have already been inactive if it was already an ancestors pair in a previous iteration. Ancestor pair occurrences are recounted as are counts of its two comprising entities, without the inactive occurrences. Note that the count of occurrences of the comprising entities is not generally reduced, but only locally reduced, in relation to the specific inter-ancestors pairs. In their relations with other entities, which are not on the $2^{nd}$ ancestors list, the ancestor entities counts and co-occurrence counts stay the same. Ancestors pair significance is re-computed, and its order in the significant pairs list is updated accordingly or removed from the list. If ancestor pairs are not significant, the pair is discarded (step 516).

In some embodiments, troubleshooting and automated evaluation of the knowledge base, source localization or pattern analysis may be done by comparing analyzed patterns to known patterns already in the knowledge base. For example, if there is a slight discrepancy in region, wherein an analyzed pattern includes a region or regions which is different than previously determined and stored patterns, if the regions are neighboring it is likely a source localization problem. Alternatively, if the regions are distant from each other, it is likely a knowledge base problem. Another example involves a correction of the knowledge base. According to the matrix knowledge base, each of two regions are either directly related, or are related via a certain number of intervening regions. If this evaluated distance at the knowledge base level is in discrepancy when compared to the identified patterns in a repetitive manner, which cannot be explained by alternative corrections (as the one suggested above to localization and others), then there is likely a knowledge base imperfection which requires correction. Yet another example is correction of the identified flow pattern analysis by higher resolution search for a specific region, which is predicted from the knowledge base and might have just fallen short of the threshold or tolerance parameters set.

Figure 21:
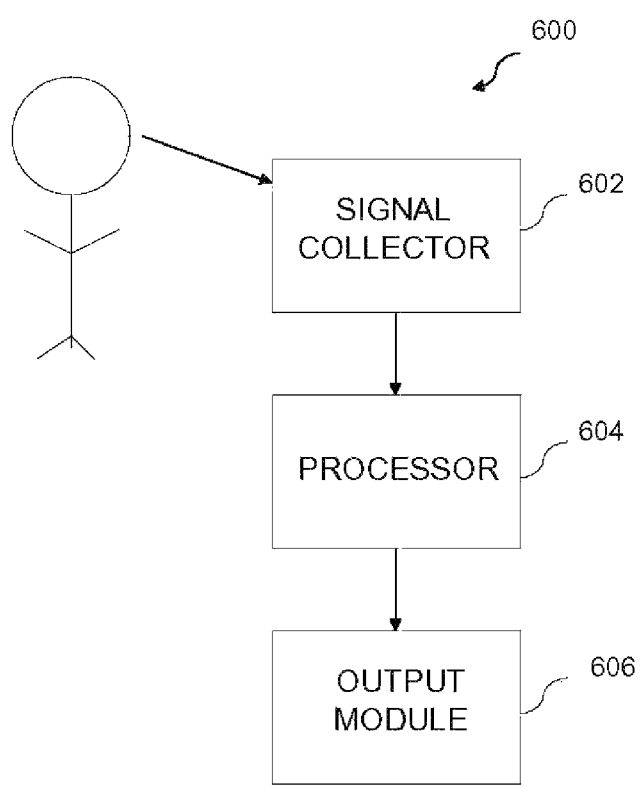
FIG. 21 is a block diagram illustration of a system for neuropsychological analysis of an individual, in accordance with embodiments of the present invention.
Figure 22:
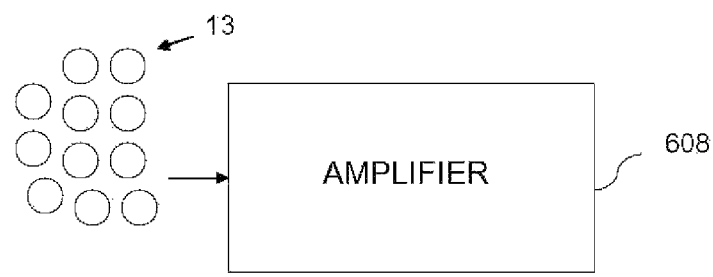
FIG. 22 is a block diagram illustration of the signal collector of FIG. 21.

The knowledge base 16 created in the manner described above is used in the system of the present invention, as will be described hereinbelow with respect to FIG. 21. Reference is now made to FIG. 21, which is a block diagram illustration of a system 600 in accordance with embodiments of the present invention. System 600 includes a signal collector 602 configured to collect signals from a testing subject 603, a processor 604 for processing the signals, and an output module 606 for displaying the results of the processed signals. Reference is now made to FIG. 22, which is a block diagram illustration of signal collector 602 shown in greater detail. In some embodiments, signal collector 602 includes electrodes 13 to be placed on the head of testing subject 603, and an amplifier 608 for amplification of signals received from electrodes 13 in response to an activity or task by testing subject 603. In some embodiments, collector 602 further includes tasks. It should be readily apparent that other types of signals may be collected and that signal collector 602 is not limited to the description herein. For example, signal collector 602 may include fMRI, PET, optical imaging, MEG or any system or method (and their combinations) for obtaining information related to brain function in a human. In some embodiments, subject 603 is not presented with particular stimuli and responses, and activity is recorded during "spontaneous activity" or during particular activities. Many such protocols of stimuli, stimuli-responses, action-related and "spontaneous" activity are known in the art, and may include any stimulus-response neuropsychological tests such as Stroop, Wis., etc; tests may include stimulus-only based tests such as mismatch negativity, BERA, etc; they may include response-only based tests, such as saccade analysis, MRP, etc; and they may include "spontaneous" activity.

Figure 23:
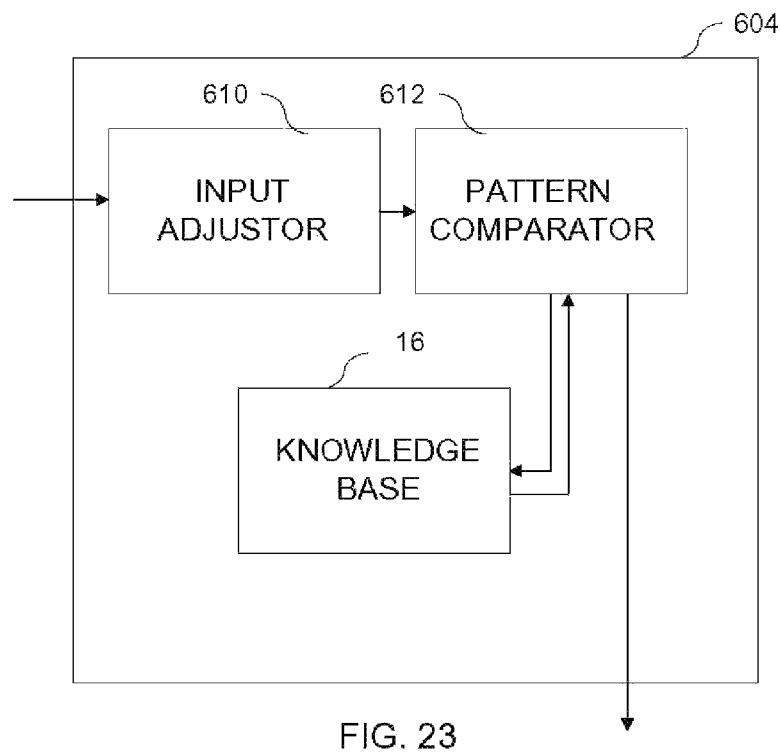
FIG. 23 is a block diagram illustration of the processor of FIG. 21.

Reference is now made to FIG. 23, which is a block diagram illustration of processor 604, showing the components in greater detail. Processor 604 includes an input adjustor 610, a pattern comparator 612 and a copy of knowledge base 16 created from experimental and published information, as described above. Input adjustor 610 is configured to adjust input from signal collector 602 so that it conforms to the flow pattern information found in knowledge base 16. Thus, in one embodiment, input adjustor 610 includes a source localizer 20 and is configured to perform source localization so as to identify regions of the brain being activated by the activity or task performed by testing subject 603. In another embodiment, input adjustor 610 is configured to identify peaks, wavelets, or other discrete identifiable elements over time for electrodes 13. In this second embodiment, the knowledge base patterns are also described at this electrode level. Pattern comparator 612 then takes the adjusted input and compares it to flow patterns included within knowledge base 16. Pattern comparator 612 is configured to identify a pathology or normal state based on comparison of the adjusted input and the stored information regarding pathological or normal patterns. Moreover, pattern comparator 612 may translate the determined patterns even if parts of the patterns do not relate to a specific pathology, by parsing the activities according to their likelihoods of matches with stored flow patterns, as will be described further hereinbelow.

In parsing, over time and as more regions are introduced, the possibilities of patterns to match up with are sharpened. Thus, for example, at a single timing with a few regions, many different patterns may fit the time-series of region activations obtained from the single subject. However with more sampled regions over time, certain patterns become more likely. It should be noted that even when particular regions or sequences of electrodes are identified, timing at the particular regions or electrodes is important in distinguishing between flow patterns. The process of parsing eventually results in a matching up of the obtained patterns with saved patterns from the database. Similarly to the above description regarding the neuropsychological analysis, the parser may work on several levels, wherein at a first level, combinations of pairs of regions are identified. At a second level, the parser identifies general behavior based on flow patterns for particular behavior sub-functions. At its most specific level, the parser can identify patterns directly relating to specific behavioral functions, such as an activity or task being performed by testing subject 603. The algorithm described with respect to the development of the research tool may also be used for neuropsychological analysis for the individual subject.

Output module 606 may be any suitable display, such as a monitor or may include graphs or reports relating to the obtained results. This information can either be used to detect effects of treatment on functional brain activity or to direct treatment, or it may be used for experimental or educational purposes. The analysis could be performed and presented offline or online during the sampling process. In one embodiment, output module 606 includes a feedback loop as part of a complete workstation (described below with reference to FIG. 24), wherein results from processor 604 are automatically used to provide additional stimuli to testing subject 603. An example of a system using a feedback loop is presented in FIG. 24, which is a block diagram illustration of system 600 in accordance with one embodiment of the present invention.

Figure 24:
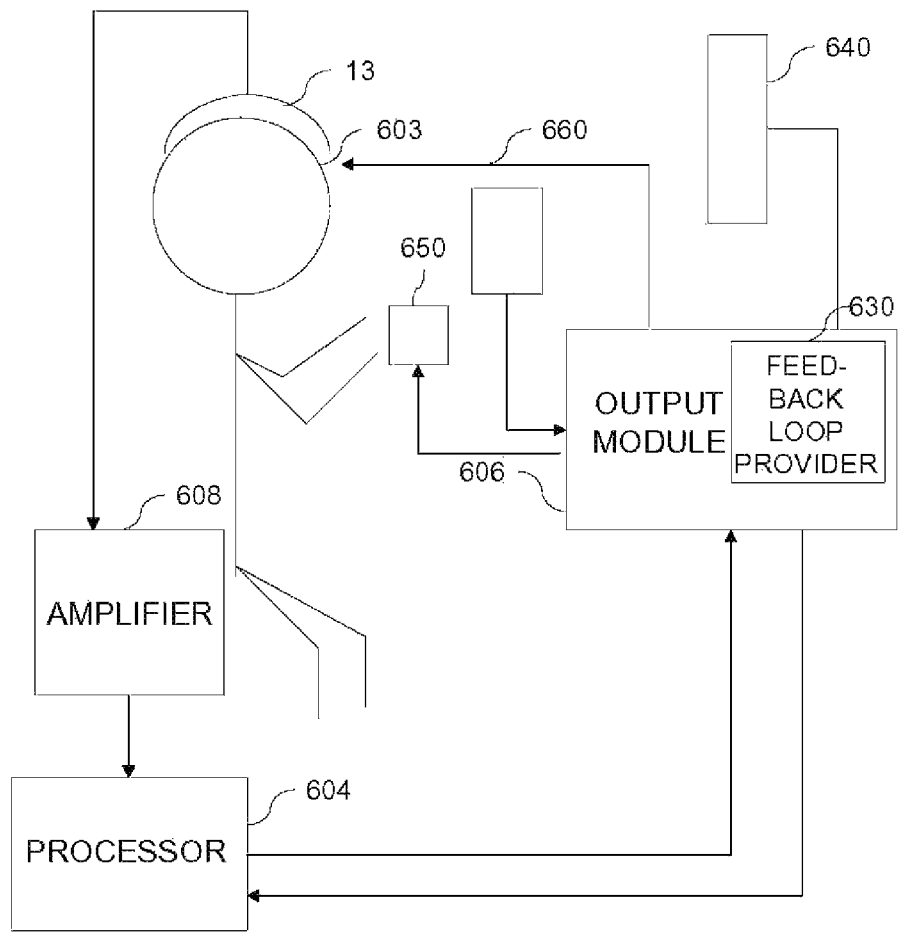
FIG. 24 is a schematic illustration of an example of a workstation for neuropsychological analysis, in accordance with embodiments of the present invention.

In the example depicted in FIG. 24, system 600 is a workstation which may enable a professional (physical or occupational therapist, speech pathologist, rehabilitation doctor, neurologist, psychiatrist etc.) to observe and direct brain effects during treatment, either with current methods or with novel methods. The workstation incorporates information regarding identified functional patterns and their change prior and during practice from the above described technology together with input regarding the treatment protocols and their peripheral effects outside the brain sampled by various technological modalities. This enables an intelligent direction of the treatment either off-line or on-line during treatment. Part of the direction is based upon peripheral biofeedback or brain neurofeedback methods, which are pattern related. Virtual reality technology may also be incorporated in the work station.

As shown in FIG. 24, system 600 could include electrodes 13 placed on the head of testing subject 603. Alternatively, any of the methods described above such as fMRI, PET, etc. could be used. Electrodes 13 are connected to amplifier 608, for amplifying signals obtained by electrodes 13, and sending the amplified signals to processor 604. Processor 604 includes pattern comparator 612 and knowledge base 16, as described above. Processor 604 provides output to output module 606, which in the present embodiment includes a feedback loop provider 630. Output module 606 with feedback loop provider 630 provides neurofeedback or peripheral feedback to subject 603 and is either a real-time on-line or alternatively off-line facilitator of stimuli wherein stimuli may be further provided or adjusted based on responses from testing subject 603. In one embodiment feedback loop provider 630 includes virtual reality technology, wherein the subject 603 may be provided with multi-sensory input either for diagnosis, treatment or both.

An example of use of a system 600 including a feedback loop provider is as follows. The subject 12 may be asked to perform a particular task. If he is unsuccessful, feedback loop provider 630 receives data showing that the task was not successfully performed. Feedback loop provider 630 may then introduce multi-sensory stimulation either simulating the task to be performed or a similar task. Testing subject 603 may then be asked again to perform the particular task. If he is unsuccessful, the same inputs may be used again. If he is partially successful, either the same or new inputs may be used to encourage further performance of the task. In this way, the neurological or psychiatric function of the brain may be restored or enhanced in certain cases, or may be compensated for by activating other areas of the brain.

Sensory input by feedback loop provider 630 may include, for example, visual input 640, somatosensory input 650, auditory input 660 or any other sensory input that may aid in restoration of neurological activity. In some embodiments, one type of sensory input is used. In other embodiments, multiple sensory inputs are provided simultaneously or sequentially. It should be readily apparent that by observing the actual flow and by correlating the flow to particular activities or pathologies, the feedback loop can be greatly facilitated.

A system such as the one described can potentially be used for many neurological and psychiatric conditions such as rehabilitation of brain injuries, treatment of neurocognitive dysfunctions and treatment of behavioral and emotional pathologies and problems. It should be noted that non-clinical applications are also ample, such as analysis of decision making, analysis of mood, analysis of personality and in general analysis of any behavioral function.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A system for brain activity analysis, the system comprising:
   an input module for receiving EEG and/or MEG signals from a subject;
   a processor, configured for identifying brain activity patterns in said signals using a counting method or method of calculating statistical significances of pairs, for identifying a plurality of candidate pathways for said brain activity patters, for defining flow patterns among functional brain regions based on candidate pathways, for accessing a flow pattern database having previously determined flow patterns, and for comparing said flow pattern to said previously determined flow patterns of said database; and
   an output module for presenting results of said comparison.

2. The system of claim 1, wherein said processor comprises a parser configured for comparing said flow pattern to said previously determined flow patterns of said database.

3. The system of claim 2, wherein said parser is configured to match patterns for a cognitive behavior.

4. The system of claim 2, wherein said parser is configured to match a particular task.

5. The system of claim 1, wherein said output module comprises a workstation including a feedback loop provider configured to receive said comparison and to provide a stimulus to the subject based on said received results.

6. The system of claim 1, wherein said signals comprise EEG signals measured using a plurality of EEG electrodes, and the processor is configured for analyzing waveforms of varying frequencies and amplitudes over time for each EEG electrode.

7. The system of claim 1, wherein said processor is configured for ranking said candidate pathways based on likelihood for a particular behavioral process, prior to said definition of said set of flow patterns, and for reducing a number of candidate pathways based on said ranking.

8. The system of claim 7, wherein said processor is configured for performing an iterative process, and wherein said reducing is based, at least in part, on previously defined flow patterns.

9. The system of claim 7, wherein said reducing is based, at least in part, on at least one temporal constraint.

10. The system of claim 1, wherein said defining said flow patterns comprises using a region matrix.

11. A method of analysis, comprising:
operating an array of EEG and/or MEG electrodes for receiving EEG and/or MEG signals from a subject;
operating a processor for identifying brain activity patterns in said signals using a counting method or method of calculating statistical significances of pairs, for identifying a plurality of candidate pathways for said brain activity patterns, for defining flow patterns among functional brain regions based on candidate pathways, for accessing a flow pattern database having previously determined flow patterns, and for comparing said flow pattern to said previously determined flow patterns of said database;
and
evaluating said subject based on said comparison.

12. The method of claim 11, wherein said at least one set of previously determined flow patterns includes multiple sets of flow patterns, each of said multiple sets corresponding to a different neuropsychological behavior.

13. The method of claim 12, wherein at least one of said multiple sets corresponds to a control group of subjects.

14. The method of claim 11, wherein said array comprises a plurality of EEG electrodes, and the method comprises analyzing waveforms of varying frequencies and amplitudes over time for each EEG electrode.

15. The method of claim 11, further comprising ranking said candidate pathways based on likelihood for a particular behavioral process, prior to said definition of said set of flow patterns, and reducing a number of candidate pathways based on said ranking.

16. The method of claim 15, wherein said obtaining said at least one flow pattern is executed iteratively, and wherein said reducing is based, at least in part, on previously defined flow patterns.

17. The method of claim 15, wherein said reducing is based, at least in part, on at least one temporal constraint.

18. The method of claim 11, wherein said defining said flow patterns comprises using a region matrix.

* * * * *

UNITED STATES PATENT AND TRADEMARK OFFICE
CERTIFICATE OF CORRECTION

PATENT NO. : 9,730,642 B2
APPLICATION NO. : 14/703913
DATED : August 15, 2017
INVENTOR(S) : Goded Shahaf et al.

It is certified that error appears in the above-identified patent and that said Letters Patent is hereby corrected as shown below:

On the Title Page

Item (73) Assignee: "Elmina Ltd." should be changed to --Elminda Ltd--

Signed and Sealed this
Twenty-sixth Day of December, 2017

Joseph Matal
*Performing the Functions and Duties of the
Under Secretary of Commerce for Intellectual Property and
Director of the United States Patent and Trademark Office*